(12) United States Patent
Weindorf et al.

(10) Patent No.: US 10,900,946 B2
(45) Date of Patent: Jan. 26, 2021

(54) PORTABLE APPARATUS FOR LIQUID CHEMICAL CHARACTERIZATION

(71) Applicant: Texas Tech University System, Lubbock, TX (US)

(72) Inventors: David Weindorf, Lubbock, TX (US); Delaina Pearson, Greenville, SC (US); Somsubhra Chakraborty, West Bengal (IN)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/715,374

(22) Filed: Dec. 16, 2019

(65) Prior Publication Data
US 2020/0141917 A1 May 7, 2020

Related U.S. Application Data

(60) Division of application No. 16/165,472, filed on Oct. 19, 2018, now Pat. No. 10,697,953, which is a (Continued)

(51) Int. Cl.
*G01J 3/00* (2006.01)
*G01N 33/24* (2006.01)
(Continued)

(52) U.S. Cl.
CPC .......... *G01N 33/246* (2013.01); *G01J 3/4406* (2013.01); *G01N 21/274* (2013.01);
(Continued)

(58) Field of Classification Search
CPC .. G01N 21/39; G01N 21/3504; G01N 21/031; G01N 2021/399; G01J 3/42
(Continued)

(56) References Cited

U.S. PATENT DOCUMENTS 6,697,665 B1    2/2004  Rava et al.
2004/0186383 A1 9/2004  Rava et al.
(Continued)

OTHER PUBLICATIONS

Weindorf, D.C. et al. "Direct soil gypsum quantification via portable X-ray fluorescence spectrometry." Soil Sci. Soc. Am. j. 2013b, 77, 2071-2077.
(Continued)

*Primary Examiner* — Md M Rahman
(74) *Attorney, Agent, or Firm* — Daniel J. Chalker; Edwin S. Flores; Chalker Flores LLP

(57) ABSTRACT

An apparatus or method determines a salinity or metal content a liquid sample by scanning the liquid sample using a PXRF spectrometer, receiving a PXRF spectra from the PXRF spectrometer, baseline correcting and smoothing the received PXRF spectra, extracting a Kα emission line of one or more elements from the baseline corrected and smoothed PXRF spectra using only one beam from the PXRF spectrometer, determining the salinity or the metal content of the liquid sample using the one or more processors and a predictive model that relates the Kα emission line of the one or more elements to the salinity or the metal content of the liquid sample, and providing the salinity or the metal content of the liquid sample to the one or more input/output interfaces.

27 Claims, 13 Drawing Sheets

Related U.S. Application Data continuation-in-part of application No. 15/319,816, filed as application No. PCT/US2015/036537 on Jun. 15, 2015, now Pat. No. 10,107,770.

(60) Provisional application No. 62/013,692, filed on Jun. 18, 2014, provisional application No. 62/575,498, filed on Oct. 22, 2017.

(51) Int. Cl.
| | |
|---|---|
| G01N 23/223 | (2006.01) |
| G01N 21/359 | (2014.01) |
| G01J 3/44 | (2006.01) |
| G01N 21/27 | (2006.01) |

(52) U.S. Cl.
CPC ......... *G01N 21/359* (2013.01); *G01N 23/223* (2013.01); *G01N 2223/076* (2013.01); *G01N 2223/304* (2013.01); *G01N 2223/33* (2013.01)

(58) Field of Classification Search
USPC ............................................. 378/47; 356/300
See application file for complete search history.

(56) References Cited

U.S. PATENT DOCUMENTS

| | | | | |
|---|---|---|---|---|
| 2012/0033220 | A1* | 2/2012 | Kotidis | G01J 3/108 356/445 |
| 2012/0158315 | A1* | 6/2012 | Trygstad | G01N 21/3577 702/25 |

OTHER PUBLICATIONS

Weindorf, D.C. et al. "Enhanced pedon horizonation using portable X-ray fluorescence spectroscopy." Soil Sci. Soc. Am. J. 2012, 76 (2), 522-531.
Wright, R.J. et al. "Atomic absorption and name emission spectrometry." In: Sparks et al. (Eds.), Methods or Soil Analysis—Part 3, Chemical Methods. Soil Science Society or America, Madison, WI, 1996, pp. 65-90.
Zhu, Y. et al. "Characterizing soils using a portable x-ray fluorescence spectrometer: 1. Soil texture." Geoderma 2011, 167-168, 167-177.
Akaike, H. "Information theory and the extension of the maximum likelihood principle." In: Petrov, V.N., Csaki, F. (Eds.), 2nd International Symposium on Information Theory. Academiai Kiadó, Budapest, 1973, pp. 267-281.
Aldabaa, A.A.A. et al. "Combination of proximal and remote sensing methods for rapid soil salinity quantification." Geoderma 2015, 239-240, 34-46.
Auchmoody, L.R., et al. "Revegetation of a brine-killed forest site." Soil Sci. Soc. Am. J. 1988, 52, 277-280.
Barreiros, M.A., et al. "Application of total-reflection XRF to elemental studies of drinking water", X-Ray Spectrom. 1997, 26, 165-168.
Berg, M. et al. "Arsenic contamination of groundwater and drinking water in Vietnam: A human health threat." Environmental Science & Technology 2001, 35(13), 2621-2626.
Bettinelli, M., et al. "Determination of heavy metals in soils and sediments by microwave-assisted digestion and inductively coupled plasma optical emission spectrometry analysis." Analytica Chimica Acta 2000, 424, 289-296.
Brevik, E.C. et al. "The past, present, and future of soils and human health studies." Soil 2015, 1, 35-46. http://dx.doi.org/10.5194/soil-1-35-2015.
Chakraborty, S., et al. "Semi-quantitative evaluation of secondary carbonates via portable X-ray fluorescence spectrometry." Soil Sci. Soc. Am. J. 2017a, 81, 844-852.
Chakraborty, S. et al. "Predicting soil arsenic pools by visible near infrared diffuse reflectance spectroscopy." Geoderma 2017a, 296, 30-37.
Chakraborty, S., et al. "Rapid assessment of regional soil arsenic pollution risk via diffuse reflectance spectroscopy." Geoderma 2017b, 289, 72-81.
Chang, C., Laird, et al. "Near infrared reflectance spectroscopy: principal components regression analysis of soil properties." Soil Sci. Soc. Am. J. 2001, 65, 480-490.
Clark, J.J.et al. "Extent, characterization, and sources of soil lead contamination in small-urban residential neighborhoods." Environ. Qual. 2014, 42, 1498-1506.
Eksperiandova, L.P., et al. "Analysis of waste water by x-ray fluorescence spectrometry." X-Ray Spectrometry 2002, 31 (3), 259-263.
Gazley, M.F., et al. "A review of the reliability and validity of portable X-ray fluorescence spectrometry (pXRF) data." In: Monograph 23, Mineral Resource and Ore Reserve Estimation, second edition AusIMM, 2014, pp. 69-82.
Hanna-Attisha, M., et al. "Elevated blood lead levels in children associated with the Flint drinking water crisis: A spatial analysis of risk and public health response." American Journal of Public Health 2016, 106(2), 283-290.
Kar, D., et al. "Assessment of heavy metal pollution in surface water." International Journal of Environmental Science & Technology 2008, 5(1), 119-124.
Koch, J., et al. "Proximal sensor analysis of mine tailings in South Africa: An exploratory study." Journal of Geochemical Exploration 2017 (Accepted; In Press) https://doi.org/10.1016/j.gexplo.2017.06.020.
Kuo, S. "Phosphorus. In: Sparks et al. (Eds.), Methods of Soil Analysis—Part 3, Chemical Methods." Soil Science Society of America, Madison, WI, 1996, pp. 869-919.
McGladdery, C. et al. "Elemental assessment of vegetation via portable Xray fluorescence (PXRF) spectrometry." J. Environ. Manage. 2018 (Accepted; In Press).
McLaren, T.I. et al. "Rapid, nondestructive total elemental analysis of Vertisol soils using portable X-ray fluorescence." Soil Sci. Soc. Am. J. 2012a, 76, 1436-1445.
McLaren, T.I. et al. "A rapid and nondestructive plant nutrient analysis using portable X-ray fluorescence." Soil Sci. Soc. Am. J. 2012, 76, 1446-1453.
Moncur, M.C. et al. "Long-term mineralogical and geochemical evolution of sulfide-rich mine tailings under a shallow water cover." Appl. Geochem. 2015, 57, 178-193.
Muggeo, V.M.R. "Segmented: an R package to tit regression models with broken-line relationships." R News 2008, 8 (1), 20-25.
Muhammad, S. et al. "Health risk assessment of heavy metals and their apportionment in drinking water of Kohistan region, northern Pakistan." Michochemical Journal 2011, 98, 334-343.
Nordstrom, D.K. "Worldwide occurrences of arsenic in ground water." Science 2002, 296 (5576), 2143-2145.
O'Rourke, S.M. et al. "An assessment of model averaging to improve predictive power of portable vis-NIR and XRF for the determination of agronomic soil properties." Geoderma 2016, 279, 31-44.
Paulette, L. et al. "Rapid assessment of soil and contaminant variability via portable x-ray fluorescence spectroscopy: Copşa Mică, Romania." Geoderma 2015, 243-244, 130-140.
Pearson, D. et al. "Water analysis via portable X-ray fluorescence spectrometry." Journal of Hydrology 2017, 544, 172-179.
Peinado, F.M. et al. "A rapid field procedure for screening trace elements in polluted soil using portable X-ray fuorescence (PXRF)." Geoderma 2010, 159, 76-82.
Pen-Mouratov, S. et al. "Influence of Industrial heavy metal pollution on soil free-living nematode population." Environ. Pollut. 2008, 152, 172-183.
Razo, I. et al. "Arsenic and heavy metal pollution of soil, water, and sediments in a semi-arid climate mining area in Mexico." Water, Air, and Soil Pollution 2004, 152, 129-152.
Reidinger, S. et al. "Rapid and accurate analyses of silicon and phosphorus in plants using a portable X-ray fluorescence spectrom-

(56) References Cited

OTHER PUBLICATIONS eter." New Phytologist 195, 699-706.Rengasamy, P., 2006. World salinization with emphasis on Australia. J. Exp. Bot. 2012, 57, 1017-1023.

Rhoades, J.D. "Salinity: electrical conductivity and total dissolved solids. In: Sparks et al. (Eds.), Methods of Soil Analysis—Part 3, Chemical Methods." Soil Science Society of America, Madison, WI, 1996, pp. 417-435.

Rodriguez-Freire, L. et al. "Post Gold King Mine spill investigation of metal stability in water and sediments of the Animas River watershed." Environmental Science and Technology 2016, 50, 11539-11548.

Royal Society of Chemistry, "Portable X-ray fluorescence analysis." Analytical Methods Committee Technical Brief No. 41. 2009, Available online at http://www.rsc.org/images/portable-x-ray-fluorescence-analysis-technical-brief-41_tcm18-214830.pdf.

Sacristán, D. et al. "Proximal sensing of Cu in soil and lettuce using portable X-ray fluorescence spectrometry." Geoderma 2016, 265, 6-11.

Salinity Laboratory Staff, 1954. Diagnosis and Improvement of Saline and Alkali Soils. Agricultural Handbook No. 60. US Department of Agriculture, Washington, DC.

Savitzky, A., et al. "Smoothing and differentiation of data by simplified least squares procedures" Anal. Chem. 1964, 36, 1627-1639.

Sharma, A. et al. "Characterizing soils via portable X-ray fluorescence spectrometer: 3. Soil reaction (pH)." Geoderma 2014, 232-234, 141-147.

Sharma, A. et al. "Characterizing soils via portable X-ray fluorescence spectrometer: 4. Cation exchange capacity (CEC)." Geoderma 2015, 239-240, 130-134.

Simon, M. et al. "Pollution of soils by the toxic spill of a pyrite mine (Aznalcollar, Spain)." Science of the Total Environment 1999, 242, 105-115.

Soltanpour, P.N. et al. "Inductively coupled plasma emission spectrometry and Inductively couple plasma-mass spectrometry." In: Sparks et al. (Eds.), Methods of Soil Analysis—Part 3, Chemical Methods. Soil Science Society of America, Madison, WI, 1996, pp. 9 1-139.

Swanhart, S. et al. "Soil salinity measurement via portable X-ray fluorescence spectrometry" Soil Sci. 2014, 179 (9). 417-423.

Trujillo-González, J.M. et al. "Heavy metal accumulation related to population density in road dust samples taken from urban sites under different land uses." Sci. Total Environ. 2016, 553, 636-642.

US Environmental Protection Agency (US-EPA). "Field portable X-ray fluorescence spectrometry for the determination of elemental concentrations in soil and sediment." 2007, Available online at: https://www.epa.gov/sites/production/files/2015-12/documents/6200.pdf (verified Sep. 20, 2016).

Vidakovic-Cifrek, Z. et al. "Cytogenetic damage in shallot (*Allium cepa*) root meristems induced by oil industry "high-density brines"". Arch. Environ. Contam. Toxicol. 2002, 43, 284-291.

Weindorf, D.C. et al. "Portable X-ray fluorescence spectrometry analysis of soils." In: Hirmas, D. (Ed.). Methods of soil analysis. Soil Science Society of America, Madison, WI. 2016, p. 1-8. doi:10.2136/methods-soil.2015.0033.

Weindorf, D.C. et al. "Advances in portable X-ray fluorescence (PXRF) for environmental, pedological, and agronomic applications." Advances in Agronomy 2014, 128, 1-45.

Weindorf, D.C. et al. "In-situ assessment of metal contamination via portable X-ray fluorescence spectroscopy: Zlatna, Romania." Environmental Pollution 2013a, 182, 92-100.

\* cited by examiner

FIG. 3A
FIG. 3B
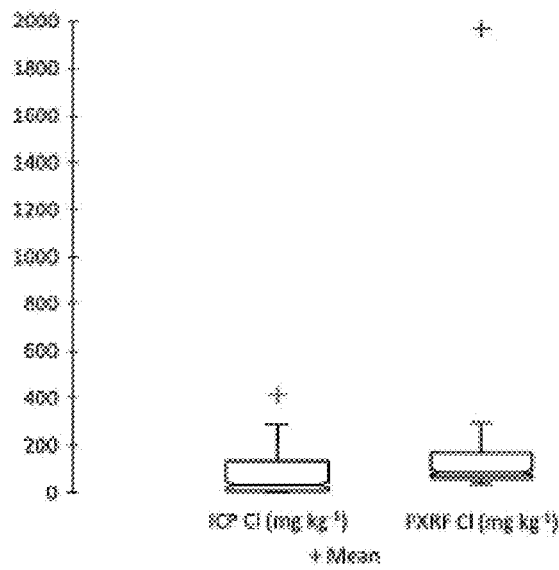
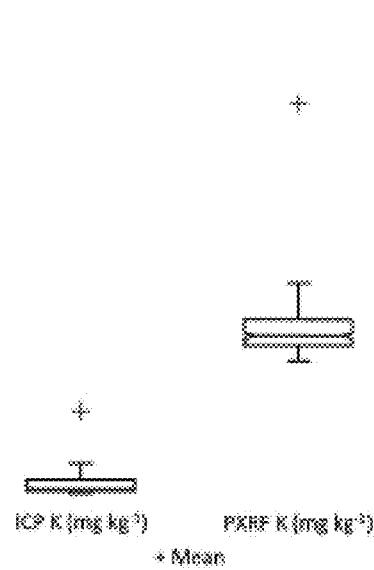
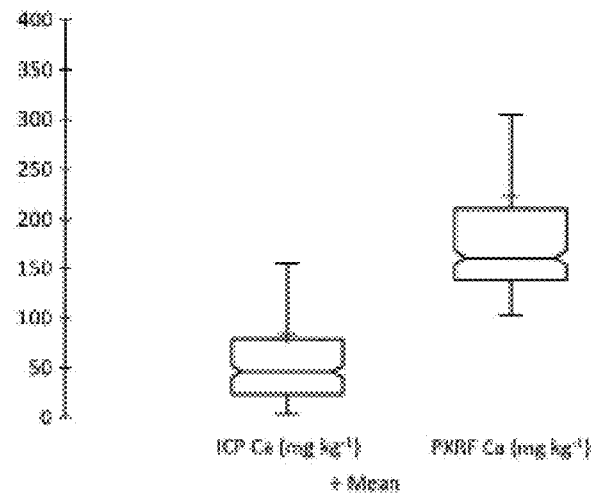
FIG. 3C

PORTABLE APPARATUS FOR LIQUID CHEMICAL CHARACTERIZATION

CROSS-REFERENCE TO RELATED APPLICATIONS

This patent application is a divisional application of U.S. patent application Ser. No. 16/165,472 filed on Oct. 19, 2018 and which claims: (1) priority to U.S. provisional patent application Ser. No. 62/575,498 filed on Oct. 22, 2017; and (2) is a continuation-in-part application of U.S. patent application Ser. No. 15/319,816 filed on Dec. 19, 2016 entitled "Portable Apparatus for Soil Chemical Characterization," now U.S. Pat. No. 10,107,770, which is a U.S. national phase application of PCT patent application PCT/US2015/036537 filed on Jun. 18, 2015, which claims priority to U.S. provisional patent application Ser. No. 62/013,692 filed on Jun. 18, 2014.

All of the foregoing patent applications are hereby incorporated by reference in their entirety.

STATEMENT OF FEDERALLY FUNDED RESEARCH

The salinity determination invention was made with government support under Agreement No. 15-CS-11011800-013 awarded by the US Forest Service. The government has certain rights in the salinity determination invention.

The metal content determination invention was not made with government support. The government does not have any rights in the metal content determination invention.

INCORPORATION-BY-REFERENCE OF MATERIALS FILED ON COMPACT DISC

None.

TECHNICAL FIELD OF THE INVENTION

The present invention relates generally to the field of chemical and, more particularly, to a portable apparatus for liquid chemical characterization using x-ray fluorescence spectrometry.

BACKGROUND OF THE INVENTION

Environmental quality assessment is of paramount importance as the world's population approaches eight billion people in the coming decades. Non-polluted soil and water for food production are among the most basic of human necessities. However, industrial development has resulted in widespread pollution and salinization of both soil and water resources (e.g., Pen-Mouratov et al., 2008; Weindorf et al., 2013a; Rengasamy, 2006; Trujillo-Gonzalez et al., 2016). For example, Auchmoody and Walters (1988) documented the impact of brine spills on soils and vegetation in the Allegheny National Forest of Northwestern Pennsylvania, noting that "brine spills and accidental discharges pose serious environmental threats." Similarly, Vidakovic-Cifrek et al. (2002) note that calcium bromide and calcium chloride are commonly prepared high-density brines used in oil exploration and production. However, they concede that accidental releases of such salts can and do pollute adjacent groundwater and soil.

Soil and water salinity are intrinsically linked as the former relies on slurries or saturated pastes whereby salts precipitated in soil dissolve into solution and are measured in the aqueous phase. Traditional analysis of water salinity has commonly used electrical conductance. For decades, the Solubridge (a rudimentary, analog salinity bridge) was the preferred technology (Salinity Laboratory Staff, 1954), whereas more recently, the use of digital conductivity meters has become commonplace. Conductivity meters rely on the fact that dissolved cations and anions in aqueous solution effectively bolster the transmission of electric current (Rhoades, 1996). Thus, the more dissolved salt present in aqueous samples, the greater the electrical conductivity (EC). However, salinity meters only provide information on the total dissolved solutes found in water; they do not identify the types of cations/anions which contribute to the salinity of the sample. Elemental identification/quantification has been reliant first upon flame photometry, then atomic absorption spectroscopy (MS) (Wright and Stuczynski, 1996), and finally inductively coupled plasma atomic emission spectroscopy (ICP-AES) (Soltanpour et al. 1996). Colorimetry and other wet chemistry techniques may also be used for the identification and qualitative estimation of certain elements (e.g., Kuo, 1996).

Applied to soil and environmental science, several methods have been established for portable X-ray fluorescence (PXRF) spectrometry use in soil, sediment, and other matrices; among them Method 6200 (US-EPA, 2007), a recently established method by the Soil Survey Staff (2014), and a method by the Soil Science Society of America (Weindorf and Chakraborty, 2016). Specific applications of PXRF for soil and environmental quality analysis include quantification of cation exchange capacity (Sharma et al. 2015), soil reaction (pH) (Sharma et al. 2014), enhanced soil horizonation (Weindorf et al. 2012), plant essential nutrients (McLaren et al. 2012), and the spatial variability of pollutants (Paulette et al. 2015; Clark and Knudsen, 2014). However, three studies in particular indicate the possible utility of PXRF for elemental determination in water samples. Weindorf et al. (2013b) used PXRF for the determination of gypsum ($CaSO_4 \cdot 2H_2O$) with Ca and Sas proxy elements for gypsum content. Using simple linear regression, PXRF-determined S and Ca predicted total gypsum content, as determined by thermogravimetry, with $R^2$ of 0.91 and 0.88, respectively. Similarly, Swanhart et al. (2014) used Cl as a proxy for saturated paste soil salinity and found a calibration $R^2$ of 0.83, with an even stronger $R^2$ of 0.90 using multiple elements and multiple linear regression. As both of these represent salts present in soil, there is reason to believe that PXRF may be effective in determining water salinity using single or multiple elements as proxies (e.g., Cl, Ca, S, K).

Moreover, water often has various elements (e.g., Ca, Mg, Cl, F) dissolved in it which pose little concern to organisms so long as concentrations are relatively low. When concentrations of dissolved salts become too high, the water is often termed brackish or salt-water. However, high concentrations of dissolved metals in water can pose a serious public health risk as such substances are commonly non-detectable without laboratory analysis. In some instances, the metals dissolved in water come from natural geologic sources. Globally, saline and sodic soils constitute 397.1 and 434.3 million ha (UN-FAO, 2016) while polluted soils are found at hundreds of thousands of sites worldwide. For example in Europe, heavy metals from smelting activities account for 34.8% of polluted soils (IASS, 2012; Paulette et al., 2015; Weindorf et al., 2013). This pollution, in turn, represents a significant threat to human health (Brevik and Sauer, 2015). More specifically, Berg et al. (2001) found As levels in raw groundwater used to supply Hanoi treatment plants often surpassed World Health Organization (WHO) limits of 10 µg L$^{-1}$, the origins of which stem from the Red River Basin. Nordstrom (2002) detailed an extensive list of countries with As-laden groundwater including Bangladesh, India, Argentina, Chile, Germany, Hungary, Romania, USA, and many others whereby As is naturally occurring from geologic sources. In other cases the metals stem from industrial pollution, mining, or waste migration into surface or subsurface waters used for drinking. For example, smelting operations in Eastern Europe left widespread metal pollution across surface soils (Paulette et al., 2015; Weindorf et al., 2013). Similarly, Razo et al. (2004) found surface water storage ponds in Villa de la Paz-Matehuala contained As levels more than five times the Mexican drinking water standard. More recently in the United States, the city of Flint, Mich. (pop. ~100,000) experienced a public health crisis when the city's water supply became contaminated with Pb (Hanna-Attisha et al., 2016). In 2015, the Gold King Mine spill in Colorado, USA released hundreds of thousands of gallons of acid mine drainage waste into the Animas River; a source of irrigation water for the farming communities of Farmington, N. Mex. and the Navajo Nation (Rodriguez-Freire et al., 2016). Some studies have also established linkages between metal content in water and other chemical factors such as pH (Muhammad et al., 2011) and conductivity (Kar et al., 2008).

The WHO (2008) has established numerous chemical limits for various elements in drinking water in order to assure human health and safety. For example, the WHO drinking water guidelines for Pb, Zn, and Cu are 10 µg L$^{-1}$, 3 mg L$^{-1}$, and 2 mg L$^{-1}$, respectively. In determining water quality, the WHO reviews a number of analytical methods, among them flame atomic absorption spectrometry (FAAS), atomic absorption spectrophotometry (AAS), electrothermal atomic absorption spectrometry (EAAS), and inductively coupled plasma mass spectroscopy (ICP-MS). By comparison, only two field methods are noted: colorimetry and absorptiometry. Thus, fewer field methods are available and with less analytical precision and accuracy, relative to laboratory approaches.

Recently, PXRF has rapidly developed as a field-portable instrument capable of producing multi-elemental data with limited sample preparation. Accuracy of PXRF generally improves with increasing atomic number, as elemental quantification is tied to electron shells which become increasingly dense as atomic number increases. The Royal Society of Chemistry (2009) provides a succinct overview of the technology whereby a miniature X-ray tube dissipating a few watts is used to excite elements, thereby causing them to generate secondary fluorescence X-rays with characteristic energies for each element. Elemental abundance is quantified via silicon drift detector (SDD), which provides "higher resolution with little degradation in spectrum quality (e.g., count rate-dependent peak broadening or drift)" relative to silicon PIN detectors (Royal Society of Chemistry, 2009). Matrix interference is caused by inter-elemental effects whereby emission line overlap and other background variation must be resolved through signal processing (Peinado et al., 2010). While PXRF is theoretically capable of determining many elements, the excitation of low atomic number elements (e.g., <K) is often problematic given fluorescence attenuation in air. Helium purge or vacuum attachments can overcome some of these limitations, but PXRF determination on low atomic number elements remains problematic (Weindorf et al., 2014). Those limitations notwithstanding, numerous methods now exist for PXRF evaluation of elements in soil and sediment (US-EPA, 2007; Soil Survey Staff, 2014). A litany of studies have established its use for soil (e.g., McLaren et al., 2012a; Zhu et al., 2011; Chakraborty et al., 2017a) and vegetal analysis (e.g., McGladdery et al., 2018; McLaren et al., 2012b; Reidinger et al., 2012). However, the evaluation of liquids by PXRF is comparatively sparse. An early study by Eksperiandova et al. (2002) evaluated wastewater by PXRF using agar and gelatin as a holding matrix for polluted waters. They obtained reasonably low relative standard deviations (up to 0.08%) for several metals at low concentrations (<400 mg L$^{-1}$). Pearson et al. (2017) extended the use of PXRF by directly determining water salinity based upon elemental determinations of brine waters in a hooded test stand. Using piecewise linear regression of PXRF sensed Cl, they obtained R$^2$ values of 0.77 (RMSE 0.95 µS cm$^{-1}$) relative to electrical conductance. Further unpublished data by Pearson et al. investigated the utility of PXRF to quantify metals in standard ICP calibration solutions. Results showed the potential for multi-elemental determination with accuracy of □ ±10% relative to certified reference values.

As a result, there is a need for a portable apparatus and method for liquid chemical characterization, namely salinity and metal content, using PXRF.

SUMMARY OF THE INVENTION

In one embodiment, the present invention includes a computerized method for determining a salinity of a liquid sample by: providing a x-ray fluorescence (PXRF) spectrometer, a probe connected to the PXRF spectrometer, one or more processors communicably coupled to the PXRF spectrometer, and one or more input/output interfaces communicably coupled to the one or more processors; scanning the liquid sample using the PXRF spectrometer; receiving a PXRF spectra from the PXRF spectrometer; baseline correcting and smoothing the received PXRF spectra; extracting a Kα emission line of one or more elements from the baseline corrected and smoothed PXRF spectra using only one beam from the PXRF spectrometer; determining the salinity of the liquid sample using the one or more processors and a predictive model that relates the Kα emission line of the one or more elements to the salinity of the liquid sample; and providing the salinity of the liquid sample to the one or more input/output interfaces. In some embodiments, the method may further include selecting the one or more element from a list of elements detectable by the PXRF spectrometer. For example, the selected elements could be one or more of Cl, K and Ca. In some embodiments, the predictive model uses a partial least squares regression (PLSR) multivariate algorithm or a support vector regression (SVR) multivariate algorithm. In some embodiments, the predictive model relates the Kα emission line of the one or more elements to the salinity of the liquid sample by: calculating a full width at half maximum (FWHM) and a maximum height (H$_{max}$) of each element peak using the Kα emission line for the element; and using the calculated FWHM and H$_{max}$ for each element peak to predict the salinity of the liquid sample. In some embodiments, the method may also include one or more of the following: placing the probe in contact with or proximate to the liquid sample; calibrating the predictive model; configuring the PXRF spectrometer to detect the salinity of the liquid sample; the scanning, receiving, baseline correcting and smoothing, extracting, determining and providing steps are performed in situ; determining a geographic location of the liquid sample using a space-based satellite navigation system; determining an elevation of the liquid sample; the scanning, receiving, baseline correcting and smoothing, extracting, determining and providing steps are performed on site proximate to where the liquid sample was taken; and/or the x-ray fluorescence (PXRF) spectrometer, the probe, the one or more processors, and the one or more input/output interfaces are integrated into a portable device.

In another embodiment, the present invention includes an apparatus having a probe, a x-ray fluorescence (PXRF) spectrometer connected to the probe, one or more processors communicably coupled to the PXRF spectrometer, and one or more input/output interfaces communicably coupled to the one or more processors. The one or more processors scan the liquid sample using the PXRF spectrometer, receiving a PXRF spectra from the PXRF spectrometer, baseline correct and smooth the received PXRF spectra, extract a Kα emission line of one or more elements from the baseline corrected and smoothed PXRF spectra using only one beam from the PXRF spectrometer, determine the salinity of the liquid sample and a predictive model that relates the Kα emission line of the one or more elements to the salinity of the liquid sample, and provide the one or more properties of the liquid sample to the one or more input/output interfaces. In some embodiments, one or more processors further select the one or more element from a list of elements detectable by the PXRF spectrometer. For example, the selected elements could be one or more of Cl, K and Ca. In some embodiments, the predictive model uses a partial least squares regression (PLSR) multivariate algorithm or a support vector regression (SVR) multivariate algorithm. In some embodiments, the predictive model relates the Kα emission line of the one or more elements to the salinity of the liquid sample by: calculating a full width at half maximum (FWHM) and a maximum height ($H_{max}$) of each element peak using the Kα emission line for the element; and using the calculated FWHM and $H_{max}$ for each element peak to predict the salinity of the liquid sample. In some embodiments, the one or more processors may also: calibrate the predictive model; configure the PXRF spectrometer to detect the salinity of the liquid sample; perform the scanning, receiving, baseline correcting and smoothing, extracting, determining and providing steps in situ; determine a geographic location of the liquid sample using a space-based satellite navigation system; and/or determine an elevation of the liquid sample. In some embodiments, the one or more input/output interfaces include a display, a data storage, a printer or a communications interface. In some embodiments, the apparatus is portable. In some embodiments, the apparatus is used on site proximate to where the liquid sample was taken.

In yet another embodiment, the present invention includes a computer program embodied on a non-transitory computer readable medium that causes one or more processors to: scan a liquid sample using a PXRF spectrometer; receive a PXRF spectra from the PXRF spectrometer; baseline correct and smooth the received PXRF spectra; extract a Kα emission line of one or more elements from the baseline corrected and smoothed PXRF spectra using only one beam from the PXRF spectrometer; determine a salinity of the liquid sample using the one or more processors and a predictive model that relates the Kα emission line of the one or more elements to the salinity of the liquid sample; and provide the salinity of the liquid sample to one or more input/output interfaces. In some embodiments, the computer program includes the features described above in reference to the method and apparatus.

In one embodiment, the present invention includes a computerized method for determining a metal content of a liquid sample by: providing a x-ray fluorescence (PXRF) spectrometer, a probe connected to the PXRF spectrometer, one or more processors communicably coupled to the PXRF spectrometer, and one or more input/output interfaces communicably coupled to the one or more processors; scanning the liquid sample using the PXRF spectrometer; receiving a PXRF spectra from the PXRF spectrometer; baseline correcting and smoothing the received PXRF spectra; extracting a Kα emission line of one or more elements from the baseline corrected and smoothed PXRF spectra using only one beam from the PXRF spectrometer; determining or the metal content of the liquid sample using the one or more processors and a predictive model that relates the Kα emission line of the one or more elements to the metal content of the liquid sample; and providing the metal content of the liquid sample to the one or more input/output interfaces. In some embodiments, the method may further include selecting the one or more element from a list of elements detectable by the PXRF spectrometer. For example, the selected elements could be one or more of Ca, Cu, Fe, K, Mn, Pb and Zn. In some embodiments, the predictive model uses a partial least squares regression (PLSR) multivariate algorithm or a support vector regression (SVR) multivariate algorithm. In some embodiments, the predictive model relates the Kα emission line of the one or more elements to the metal content of the liquid sample by: calculating a full width at half maximum (FWHM) and a maximum height ($H_{max}$) of each element peak using the Kα emission line for the element; and using the calculated FWHM and $H_{max}$ for each element peak to predict the metal content of the liquid sample. In some embodiments, the method may also include one or more of the following: placing the probe in contact with or proximate to the liquid sample; calibrating the predictive model; configuring the PXRF spectrometer to detect the metal content of the liquid sample; the scanning, receiving, baseline correcting and smoothing, extracting, determining and providing steps are performed in situ; determining a geographic location of the liquid sample using a space-based satellite navigation system; determining an elevation of the liquid sample; the scanning, receiving, baseline correcting and smoothing, extracting, determining and providing steps are performed on site proximate to where the liquid sample was taken; and/or the x-ray fluorescence (PXRF) spectrometer, the probe, the one or more processors, and the one or more input/output interfaces are integrated into a portable device.

In another embodiment, the present invention includes an apparatus having a probe, a x-ray fluorescence (PXRF) spectrometer connected to the probe, one or more processors communicably coupled to the PXRF spectrometer, and one or more input/output interfaces communicably coupled to the one or more processors. The one or more processors scan the liquid sample using the PXRF spectrometer, receiving a PXRF spectra from the PXRF spectrometer, baseline correct and smooth the received PXRF spectra, extract a Kα emission line of one or more elements from the baseline corrected and smoothed PXRF spectra using only one beam from the PXRF spectrometer, determine the metal content of the liquid sample and a predictive model that relates the Kα emission line of the one or more elements to the metal content of the liquid sample, and provide the one or more properties of the liquid sample to the one or more input/output interfaces. In some embodiments, one or more processors further select the one or more element from a list of elements detectable by the PXRF spectrometer. For example, the selected elements could be one or more of Ca, Cu, Fe, K, Mn, Pb and Zn. In some embodiments, the predictive model uses a partial least squares regression (PLSR) multivariate algorithm or a support vector regression (SVR) multivariate algorithm. In some embodiments, the predictive model relates the Kα emission line of the one or more elements to the metal content of the liquid sample by: calculating a full width at half maximum (FWHM) and a maximum height ($H_{max}$) of each element peak using the Kα emission line for the element; and using the calculated FWHM and $H_{max}$ for each element peak to predict the metal content of the liquid sample. In some embodiments, the one or more processors may also: calibrate the predictive model; configure the PXRF spectrometer to detect the metal content of the liquid sample; perform the scanning, receiving, baseline correcting and smoothing, extracting, determining and providing steps in situ; determine a geographic location of the liquid sample using a space-based satellite navigation system; and/or determine an elevation of the liquid sample. In some embodiments, the one or more input/output interfaces include a display, a data storage, a printer or a communications interface. In some embodiments, the apparatus is portable. In some embodiments, the apparatus is used on site proximate to where the liquid sample was taken.

In yet another embodiment, the present invention includes a computer program embodied on a non-transitory computer readable medium that causes one or more processors to: scan a liquid sample using a PXRF spectrometer; receive a PXRF spectra from the PXRF spectrometer; baseline correct and smooth the received PXRF spectra; extract a Kα emission line of one or more elements from the baseline corrected and smoothed PXRF spectra using only one beam from the PXRF spectrometer; determine a metal content of the liquid sample using the one or more processors and a predictive model that relates the Kα emission line of the one or more elements to the metal content of the liquid sample; and provide the metal content of the liquid sample to one or more input/output interfaces. In some embodiments, the computer program includes the features described above in reference to the method and apparatus.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which:

FIG. 3A-3C are box and whisker plots showing elemental concentrations of Cl (FIG. 3A), K (FIG. 3B), and Ca (FIG. 3C) in water samples as derived from both inductively coupled plasma (ICP) atomic emission spectroscopy and portable X-ray fluorescence (PXRF) spectrometry showing the first quartile, second quartile, median, third quartile, fourth quartile, and mean values;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Note that these terms may be used interchangeable without limiting the scope of the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
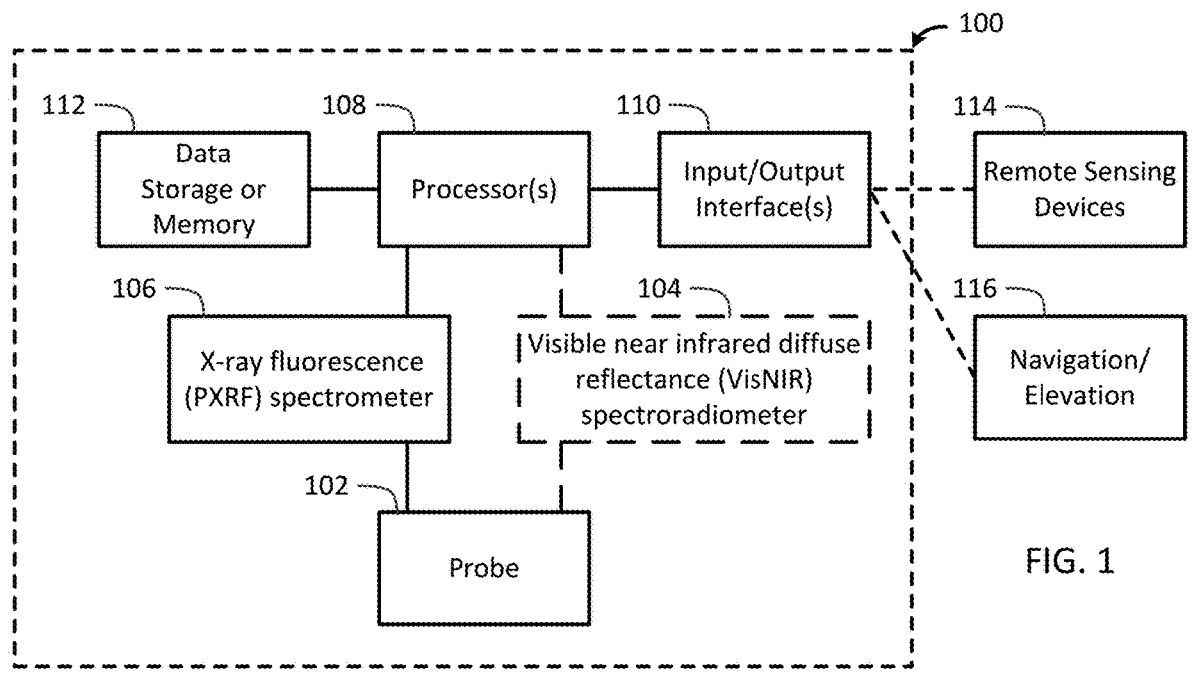
FIG. 1 is a block diagram of an apparatus in accordance with one embodiment of the present invention.

Now referring to FIG. 1, a block diagram of an apparatus 100 in accordance with one embodiment of the present invention is shown. The apparatus 100 includes a probe 102, a x-ray fluorescence (PXRF) spectrometer 106 connected to the probe 102, one or more processors 108 communicably coupled to the PXRF spectrometer 106, and one or more input/output interfaces 110 communicably coupled to the one or more processors 108. In some embodiments, the apparatus 100 may include a visible near infrared diffuse reflectance (VisNIR) spectroradiometer 104 connected to the probe 102 and communicably coupled to the one or more processors 108 (see U.S. patent application Ser. No. 15/319,816 filed on Dec. 19, 2016 entitled "Portable Apparatus for Liquid Chemical Characterization"). The one or more processors 108 scan the liquid sample using the PXRF spectrometer 106, receive a PXRF spectra from the PXRF spectrometer 106, baseline correct and smooth the received PXRF spectra, extract a Kα emission line of one or more elements from the baseline corrected and smoothed PXRF spectra using only one beam from the PXRF spectrometer 106, determine the salinity or the metal content of the liquid sample using the one or more processors 108 and a predictive model that relates the Kα emission line of the one or more elements to the salinity or the metal content of the liquid sample, and provide the salinity or the metal content of the liquid sample to the one or more input/output interfaces 110. The apparatus 100 can be portable such that the one or more processors 108 perform the scanning, receiving, baseline correcting and smoothing, extracting, determining and providing steps in situ. Moreover, the scanning, receiving, baseline correcting and smoothing, extracting, determining and providing steps can be performed on site proximate to where the liquid sample was taken.

The one or more processors 108 may transmit or receive data wirelessly via the one or more input/output interfaces 110. The one or more input/output interfaces 110 can be any type of wired or wireless interface to other components, devices or systems either remote or locally located to the apparatus 110. The one or more input/output interfaces 110 may be a display, a data storage, a printer, a communications interface, etc. The one or more processors 108 may automatically selecting the one or more element from a list of elements detectable by the PXRF spectrometer 106 (as specified by the PXRF spectrometer manufacturer now or in the future), or receive such selection(s) from the one or more input/output interfaces 110. For example, the selected elements could be one or more of Cl, K and Ca whenever the salinity of the liquid sample is to be determined, or one or more of Ca, Cu, Fe, K, Mn, Pb and Zn whenever the metal content of the liquid sample is to be determined.

The one or more processors 108 may also receive data from a remote sensing device 114, such as a satellite (e.g., Landsat 7, Landsat 8, etc.). For example, the one or more processors 108 may determine a geographic location of the liquid sample using a space-based satellite navigation system 116 or an elevation of the liquid sample.

The one or more processors 108 may also calibrate the predictive model, configure the PXRF spectrometer to detect the salinity or the metal content of the liquid sample, etc. The predictive model can use a partial least squares regression (PLSR) multivariate algorithm or a support vector regression (SLR) multivariate algorithm. In addition, the predictive model can relate the Kα emission line of the one or more elements to the salinity or the metal content of the liquid sample by: (1) calculating a full width at half maximum (FWHM) and a maximum height ($H_{max}$) of each element peak using the Kα emission line for the element; and using the calculated FWHM and $H_{max}$ for each element peak to predict the salinity or the metal content of the liquid sample.

Figure 2:
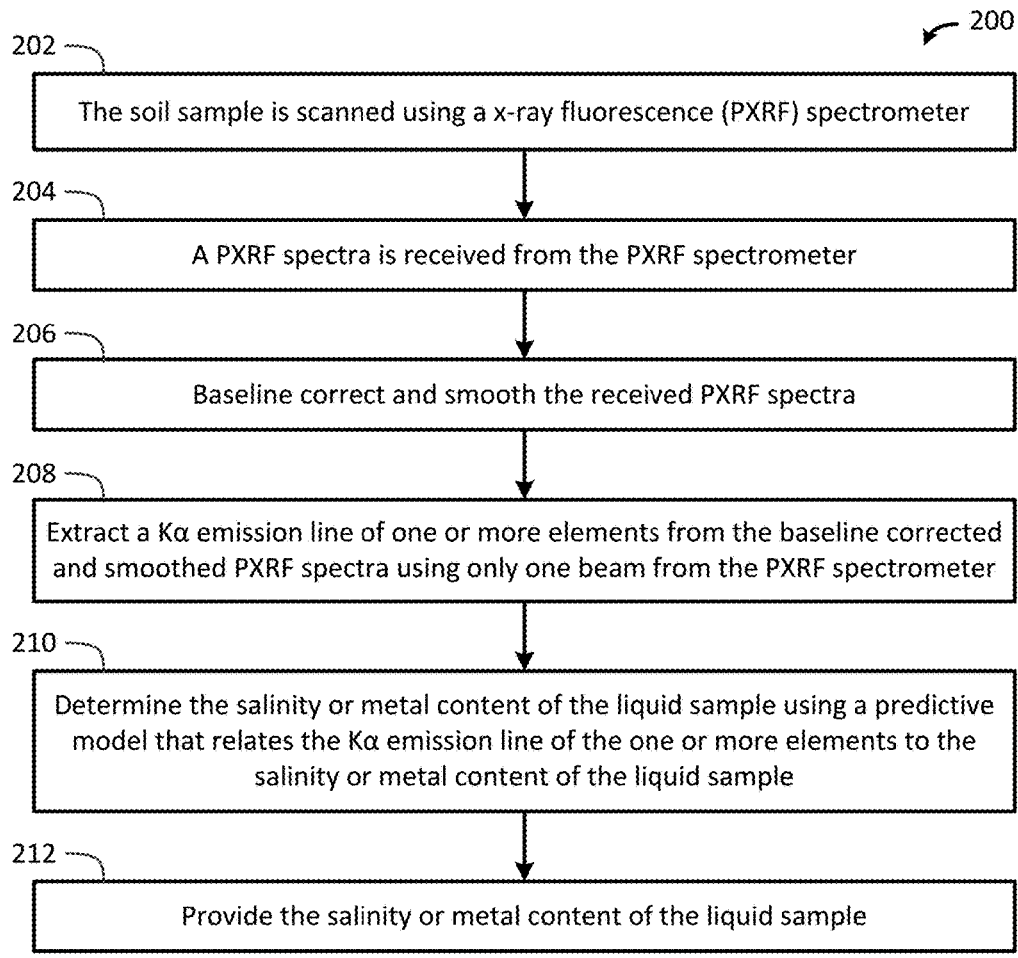
FIG. 2 is a flow chart of a method in accordance with one embodiment of the present invention.

Referring now to FIG. 2, a flow chart of a computerized method 200 for determining a salinity or metal content of a liquid sample in accordance with one embodiment of the present invention is shown. The method is performed using an apparatus as shown in FIG. 1 or other suitable systems, devices or components. The liquid sample is scanned using a x-ray fluorescence (PXRF) spectrometer in block 202. A PXRF spectra is received from the PXRF spectrometer in block 204. The received PXRF spectra is baseline corrected and smoothed in block 206. Extract a Kα emission line of one or more elements from the baseline corrected and smoothed PXRF spectra using only one beam from the PXRF spectrometer in block 208. Determine the salinity or the metal content of the liquid sample using the one or more processors and a predictive model that relates the Kα emission line of the one or more elements to the salinity or the metal content of the liquid sample in block 210. The salinity or metal content of the liquid sample are provided to one or more input/output interfaces in block 212. The scanning, receiving, baseline correcting and smoothing, extracting, determining and providing steps can be performed in situ. Moreover, the scanning, receiving, baseline correcting and smoothing, extracting, determining and providing steps can be performed on site proximate to where the liquid sample was taken. The foregoing method can be performed by a computer program embodied on a non-transitory computer readable medium.

The one or more elements can be selected, automatically or manually, from a list of elements detectable by the PXRF spectrometer (as specified by the PXRF spectrometer manufacturer now or in the future). For example, the selected elements could be one or more of Cl, K and Ca whenever the salinity of the liquid sample is to be determined, or one or more of Ca, Cu, Fe, K, Mn, Pb and Zn whenever the metal content of the liquid sample is to be determined. The predictive model can use a partial least squares regression (PLSR) multivariate algorithm or a support vector regression (SLR) multivariate algorithm. In addition, the predictive model can relate the Kα emission line of the one or more elements to the salinity or the metal content of the liquid sample by: (1) calculating a full width at half maximum (FWHM) and a maximum height ($H_{max}$) of each element peak using the Kα emission line for the element; and using the calculated FWHM and $H_{max}$ for each element peak to predict the salinity or the metal content of the liquid sample.

Additional steps may include: (1) placing the probe in contact with or proximate to the liquid sample; (2) calibrating the predictive model; (3) configuring the PXRF spectrometer to detect the salinity or the metal content of the liquid sample; (4) determining a geographic location of the liquid sample using a space-based satellite navigation system; (5) determining an elevation of the liquid sample; and/or (6) any other desired step.

The present invention demonstrates that proximal or remotely sensed data can be efficiently used as a proxy for liquid salinity or metal content assessment, which could result in substantial cost savings relative to traditional lab salinity and metal content measurements. However, liquid salinity and metal content are only two example of how the present invention can be used.

A non-limiting example of using the present invention to predict surface soil salinity was described U.S. patent application Ser. No. 15/319,816 filed on Dec. 19, 2016 entitled "Portable Apparatus for Liquid Chemical Characterization," now U.S. Pat. No. 10,107,770, which is hereby incorporated by reference in its entirety.

Another non-limiting example of using the present invention to determine liquid salinity will now be described. The PXRF does present certain limitations (Weindorf et al., 2014) which need to be considered for aqueous sample assessment. Moisture is known to denude the fluorescent energy of various elements, potentially interfering with accuracy (Weindorf et al., 2014). Also suspended sediments, themselves rife with abundant elements, would likely bias PXRF results. However, the use of specialized films (e.g., Prolene® thin-film) with maximum fluorescence transmissivity and filtration/centrifugation of samples to remove any suspended sediments would seem logical means toward overcoming such limitations. Pearson et al. (2017) extended the use of PXRF by directly determining water salinity based upon elemental determinations of brine waters in a hooded test stand. Using piecewise linear regression of PXRF sensed Cl, they obtained $R^2$ values of 0.77 (RMSE 0.95 μS cm⁻¹) relative to electrical conductance. Further unpublished data by Pearson et al. investigated the utility of PXRF to quantify metals in standard ICP calibration solutions. Results showed multi-elemental determination with accuracy of ~±10% relative to certified reference values.

Given the number of polluted and/or salt impacted waters found worldwide, the evaluation of PXRF as a rapid analytical technique for aqueous samples appears timely. If proven accurate for the assessment and quantification of dissolved solutes, it could be an important step toward consideration of more advanced aqueous chemistries inclusive of pollutants (e.g., heavy metals) and suspended solids. As such, the objective of the following research was to evaluate using PXRF in predicting water EC. As shown below, PXRF successfully detects elements which can be used to predict water salinity and show strong correlation to electrical conductivity data across a wide range of salinity concentrations.

Rapid, in-situ elemental water analysis would be an invaluable tool in studying polluted and/or salt-impacted waters. Analysis of water salinity has commonly used electrical conductance (EC); however, the identity of the elements responsible for the salinity are not revealed using EC. Several studies have established the viability of using portable X-ray fluorescence (PXRF) spectrometry for elemental data analysis of soil, sediment, and other matrices (e.g., see the above-referenced patent application). However, the accuracy of PXRF is known to be affected while scanning moisture-laden soil samples. But the study described below used PXRF elemental data in water samples to predict water EC. A total of 256 water samples, from 10 different countries were collected and analyzed via PXRF, inductively coupled plasma atomic emission spectroscopy (ICP-AES), and a digital salinity bridge. The PXRF detected some elements more effectively than others, but overall results indicated that PXRF can successfully predict water EC via quantifying Cl in water samples (validation $R^2$ and RMSE of 0.77 and 0.95 log μS cm⁻¹, respectively). These findings elucidated the use of PXRF for future analysis of pollutant and/or metal contaminated waters.

The 256 water samples were collected from 10 different countries in 2015 and 2016 as follows: Belgium (1), Bolivia (5), Brazil (10), Curacao (3), Honduras (3), Italy (10), Mexico (8), Romania (8), Trinidad (1), and United States (207). Samples from within the United States were collected from Alaska (5), Arkansas (9), Arizona (35), California (1), Colorado (17), Florida (6), Minnesota (1), Mississippi (5), Nevada (14), New Mexico (40), Oklahoma (8), Texas (30), Tennessee (1), Utah (28), and Wyoming (7). Waters collected were as follows: lake (71), swimming pool (7), river (64), sea (3), tap (84), and well (27). Each sample was placed in a new 120 ml plastic bottle, sealed, and refrigerated at 4° C. prior to analysis. Samples were transported to the Pedology laboratory at Texas Tech University (Lubbock, Tex., USA) for analysis.

Prior to analysis, samples were allowed to return to room temperature (20° C.). Most samples contained no visually observable suspended solids; for those few samples that did, filtration and centrifugation was undertaken prior to analysis. Electrical conductance was measured with a Traceable™ expanded range digital conductivity meter (Fisher Scientific, Hampton, N.H., USA). The conductance probe was thoroughly washed with deionized water between samples. Performance of the salinity bridge was assured via assessment of standard conductance solutions.

Prior to PXRF analysis, each sample was placed in a Series 1400 plastic sample cup (Chemplex Industries, Palm City, Fla., USA), then covered with Prolene® thin-film (Chemplex Industries, Palm City, Fla., USA). A Delta Premium (DP-6000) PXRF (Olympus-Innov-X; Waltham, Mass., USA), was used to conduct the analyses. Prior to scanning the PXRF was calibrated with a standard 316 metal alloy target placed in front of the aperture. Once a calibration check with the alloy was successful, the instrument was positioned into a proprietary test stand for scanning; the test stand shields the operator from any errant X-radiation. Samples were positioned on the sample stage such that the water was placed directly over the PXRF aperture. The PXRF was operated in Soil Mode, a configuration capable of scanning ~25 different elements. In Soil Mode, each of the three beams was configured to scan for 30 s such that one complete scan of a given sample was completed in 90 s. Beams one and two were both operated at 40 keV, while beam three was operated at 15 keV. Two types of data were downloaded from the instrument following scanning: (1) elemental data (as reported by the software as configured), and (2) raw spectral data reporting counts and fluorescent energy (keV) for each scan. The former is a simpler approach for "off the shelf" application, while the latter provides data for advanced spectral analysis. While the PXRF can detect multiple elements simultaneously, concentrations below the detection limit are problematic as they cause discontinuity in the number of samples across the dataset. In this study, many elements were uniquely identified in different water samples, but only Ca, Cl, and K were reported continuously across all samples.

Samples were also subjected to inductively coupled plasmas atomic emission spectroscopy (ICP-AES) analysis via a Genesis model instrument (Spectro Analytical Instruments, Irvine, Calif., USA) (Soltanpour et al., 1996). Elemental data reported via ICPAES included: Al, As, B, Cd, Ca, Cl, Cu, Fe, K, Pb, Mg, Mn, Mo, Na, Ni, P, S, Se, and Zn.

Separately, two different calibration curves were constructed using reagent grade KCl and NaCl mixed with deionized water. Concentrations were set as follows: 0.001%, 0.01%, 0.05%, 0.10%, 0.50%, 1%, 2%, and 5%. These standard solutions were evaluated for electrical conductance, and for elemental concentration via both PXRF and ICP.

In this study, water EC predictive models were built with PXRF sensed elements using R 2.11.0 (R Development Core Team, 2014). The normality of EC residuals was checked by the Shapiro-Wilk test. Notably, EC values were positively skewed (Pearson skewness coefficient 4.53), while Box-Cox conversion (Box and Cox, 1964) using log transformed EC values were able to conform the data to a normal distribution. Further, the three PXRF measured elements (Cl, K, and Ca) were log transformed. Principal component analysis (PCA) was executed via R version 2.11.0 using the 'prcomp' function to visualize the clustering of water samples from different sources. Optimal number of principal components (PC) was decided from a screeplot.

Piecewise linear regression (PLR) was employed to model water EC using three PXRF measured elements (Cl, K and Ca). A few observations with missing values were deleted a priori and the rest (n=252) were randomly split into training set (176 samples, ~70%) and test set (76 observations, ~30%). PLR, also known as segmented regression, partitions the explanatory variable into intervals and fits line segments to each interval. The boundaries between the intervals are called the breakpoints. Like nonlinear regression, PLR is particularly useful to model an abrupt change of relationship between a response and a predictor. However, since the linear model is fitted for each interval, the fitted PLR model can be easily presented by equations and is therefore highly interpretable. In this study, the PLR was used with only one breakpoint for PXRF-measured Cl, K, and Ca. The location of the breakpoint, intercept, and slopes were chosen to minimize the sum of squared errors (SSE). In this study, the PLR was executed by using the segmented package (version: 0.5-1.4) in R, produced by Muggeo (2008). Model predictability was compared via $R^2$, RMSE, Akaike information criterion (AJC) and Bayesian information criterion (BIC) values (Akaike, 1973). In general, the best models show the smallest AIC and BIC values.

Furthermore, PXRF spectra were baseline corrected and smoothed using a Savitzky-Golay first order polynomial via Unscrambler®X 10.3 (CAMO Software Inc., Woodbridge, N.J.). PXRF Kα emission lines of Cl (2.62 keV), K (3.31 keV), and Ca (3.69 keV) were separated using only Beam 3 (15 keV) under Soil Mode. The method proposed by Sacristan et al. (2016) was used. Thereafter, the full width at half maximum (FWHM) and the maximum height ($H_{max}$) of Cl, K, and Ca peaks were calculated using Origin pro (Originlab, MA, USA) for their subsequent use to predict water EC.

Summary statistics of different parameters of assayed water samples are presented in Table 1 below. As expected, results exhibited substantial variation in the EC of analyzed water samples, from very low (1.33 µS cm$^{-1}$) to extremely high (157600.00 µS cm$^{-1}$), with a mean value of 7837.55 µS cm$^{-1}$ (Table 1). Notably, this study was based on a factory calibrated PXRF instrument in Soil Mode which showed several folds higher elemental concentration for Cl, K, and Ca than ICP-based results despite exhibiting reasonable agreement between PXRF and ICP results (Table 2; FIGS. 3A-3C). This variation was perhaps due to the SoilMode calibration which is not targeted to a water matrix. Moreover, higher elemental enrichment in water may have led to excessive self-absorption. Thus, it can be concluded that there is need for reliable standards focusing on water matrix to reduce this variation.

Figure 4B:
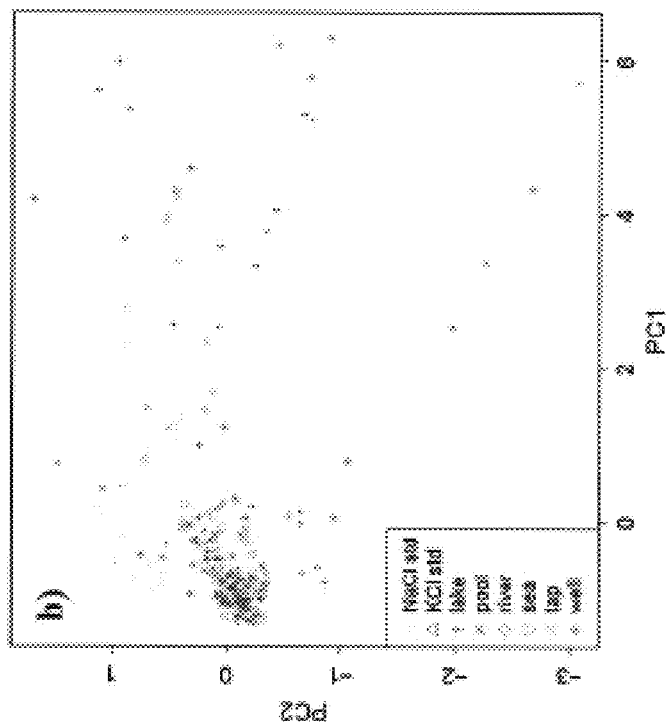
FIGS. 4A-4B are a screen plot showing proportion of variance explained by principal components (FIG. 4A), and a PC1 vs. PC2 score plot exhibiting source-wise water sample clustering (FIG. 4B)
Figure 4A:
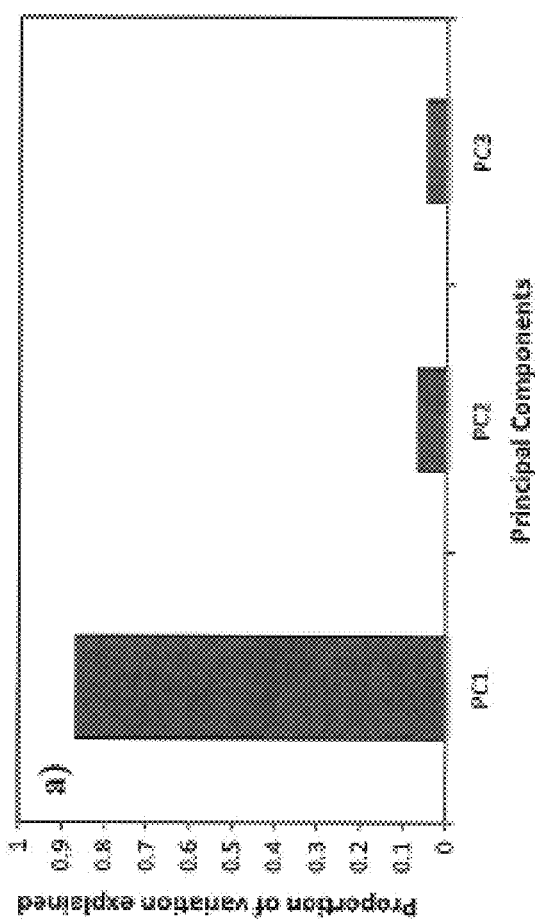

Principal component analysis was applied to the PXRF reported Cl, K, and Ca concentrations (FIGS. 4A-4B). The first two leading PCs constituted over 95% of the elemental variation (FIG. 4A), implying that using a PC1 vs PC2 plot was adequate to describe the variations among three PXRF variables (FIG. 4B). While PC1 was dominated by the PXRF-Cl (loading coefficient: 0.91), PC2 was dominated by the difference between PXRF-Ca and PXRF-K. The PC1 vs PC2 plot produced certain clustering of data, so that differentiation between water sources was readily apparent. For instance, while samples from sea showed close clustering, lake and well water samples were highly spread out along PC1, indicating that lake and well samples had large variations among PRXF-Cl (51-56,739 mg kg$^{-1}$ and 48-300 mg kg$^{-1}$ for lake and well samples, respectively). While comparing lake and well water samples, lake samples had relatively large PC2 scores, indicating a larger difference between PRXF-Ca and PRXF-K. Moreover, pool samples had relatively low PRXR-Cl contents, since they exhibited smaller values along PC1. Notably, tap water samples appeared well-mixed with lake samples. KCl-standard samples were clustered together, while NaCl-standards were relatively spread out. In general, well water samples appeared to be away from most of the other samples from different sources. Importantly, the PC score plot indicated the compositional differences between water samples from different sources.

Figure 5A:
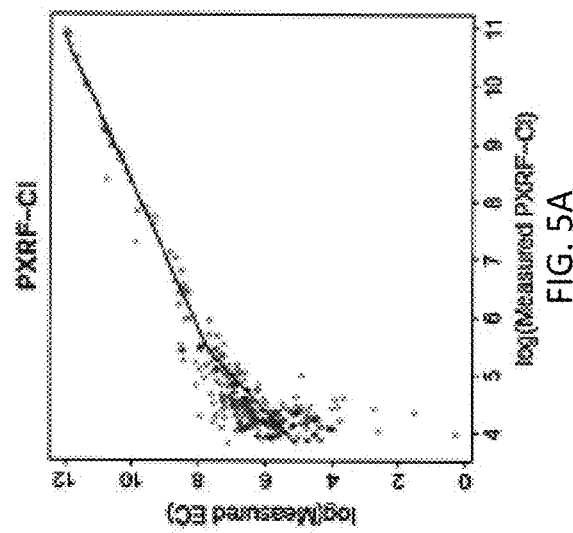
FIGS. 5A-5C are scatter plots of water EC values with added fitted line{s} from piecewise linear regression using PXRF elemental data.
Figure 5B:
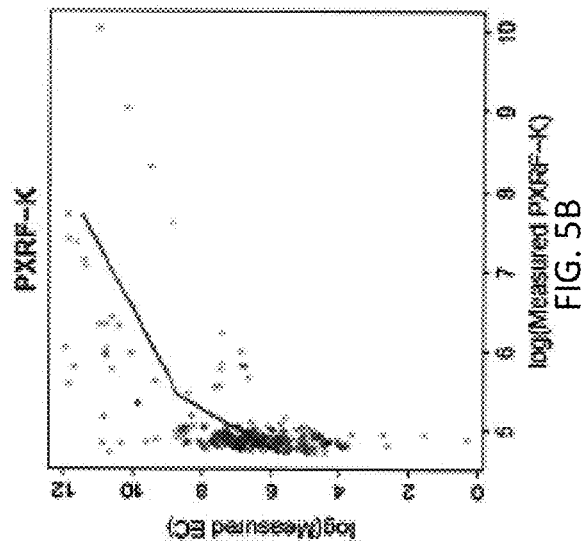
Figure 5C:
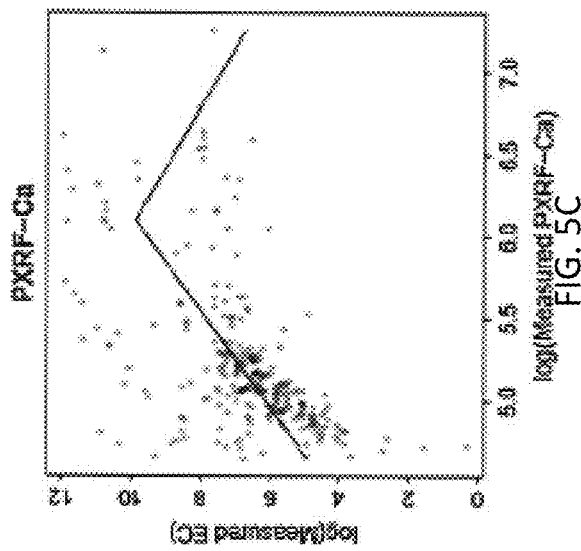

By observing the scatter plots with added fitted line(s) from the models (FIGS. 5A-5C), the use of 2-segmented PLR for calibrating soil EC with PXRF elements seemed prudent since most of the time soil or water-elemental associations represent intricate groupings of linear segments of variable slope. Overall, the EC was estimated with good accuracy with PXRF-Cl (calibration $R^2$=0.77, calibration RMSE=0.89 log µS cm$^{-1}$) (Table 3), which has been noted before elsewhere (Swanhart et al., 2014). Validation results very much followed the calibration outcomes with identical coefficient of determination (0.77) and close validation RMSE (0.95 log µS cm$^{-1}$), implying high enrichment of chloride salts in water samples. While the water EC prediction results were not as high as that obtained for soil EC using PXRF-Cl (Swanhart et al., 2014), the results were encouraging, considering the matrix interference, denudation of the fluorescent energy of various elements by water, and that ~10% of the water Cl contents were either close to or less than the detection limit of PXRF (60-100 ppm), enhancing the standard error of measurements. Contrariwise, no reasonable agreements were found between EC and PXRF-K (calibration $R^2$=0.41, calibration RMSE=1.41 log µS cm$^{-1}$) and Ca (calibration $R^2$=0.41, calibration RMSE=1.40 log µS cm$^{-1}$), possibly due to matrix effects. Furthermore, PXRF-Cl model was considered preferable

TABLE 1

Summary statistics of water EC, PXRF sensed elements and ICP measured elements.

| Parameter | n | Minimum | Maximum | Mean | Std. deviation |
|---|---|---|---|---|---|
| EC (µS cm$^{-1}$) | 252 | 1.33 | 157500.00 | 7837.55 | 24046.46 |
| ICP Cl (mg kg$^{-1}$) | 252 | 0.10 | 3688.79 | 413.33 | 957.03 |
| PXRF Cl (mg kg$^{-1}$) | 252 | 45.00 | 56739.00 | 1968.07 | 2625.02 |
| ICP K (mg kg$^{-1}$) | 252 | 0.31 | 846.45 | 69.90 | 179.09 |
| PXRF K (mg kg$^{-1}$) | 252 | 113.00 | 22901.00 | 331.15 | 1557.70 |
| ICP Ca (mg kg$^{-1}$) | 252 | 4.55 | 1105.17 | 84.03 | 131.45 |
| PXRF Ca (mg kg$^{-1}$) | 252 | 104.00 | 1410.00 | 224.85 | 174.34 |

TABLE 2

Pearson's correlation matrix of PXRF sensed elements and ICP masured elements.

| Variables | ICP Cl (mg kg$^{-1}$) | PXRF Cl (mg kg$^{-1}$) | ICP K (mg kg$^{-1}$) | PXRF K (mg kg$^{-1}$) | ICP Ca (mg kg$^{-1}$) | PXRF Ca (mg kg$^{-1}$) |
|---|---|---|---|---|---|---|
| ICP Cl (mg kg$^{-1}$) | 1[a] | | | | | |
| PXRF Cl (mg kg$^{-1}$) | 0.69 | 1 | | | | |
| ICP K (mg kg$^{-1}$) | 0.71 | 0.61 | 1 | | | |
| PXRF K (mg kg$^{-1}$) | 0.34 | 0.22 | 0.20 | 1 | | |
| ICP Ca (mg kg$^{-1}$) | 0.32 | 0.24 | 0.32 | −0.031 | 1 | |
| PXRF Ca (mg kg$^{-1}$) | 0.33 | 0.39 | 0.22 | 0.006 | 0.60 | 1 |

[a]Values in bold are different from 0 with a significant level alpha = 0.05.

with deference to model accuracy (Table 3), due to its comparatively lower AIC (468.74) and BIC (484.59) values. Owing to PXRF's inability to directly quantify Na+ because of its small, stable electron cloud, acceptable agreement between PXRF-Cl and water EC justified the possible incidences of halite (NaCl) in water samples (Aldabaa et al., 2015).

TABLE 3

Water EC model statistics using PXRF measured elements as predictors.

| Predictor (log transformed) | Model[a] | Calibration $R^2$ | $RMSE_{cali}$[b] (log µS cm$^{-1}$) | Validation $R^2$ | $RMSE_{vali}$[c] (log µS cm$^{-1}$) | AIC[d] | BIC[e] |
|---|---|---|---|---|---|---|---|
| PXRF Cl (mg kg$^{-1}$) | PLR | 0.77 | 0.89 | 0.77 | 0.95 | 468.74 | 484.59 |
| PXRF K (mg kg$^{-1}$) | PLR | 0.41 | 1.41 | 0.31 | 1.65 | 630.65 | 646.50 |
| PXRF Ca (mg kg$^{-1}$) | PLR | 0.41 | 1.40 | 0.18 | 1.81 | 628.67 | 644.52 |

[a]PLR, placewise linear regression.
[b]$RMSE_{cali}$, root mean squared error of calibration.
[c]$RMSE_{vali}$, root mean squared error of validation.
[d]AIC, information criterion.
[e]BIC, Bayesian information criterion.

Figure 6A:
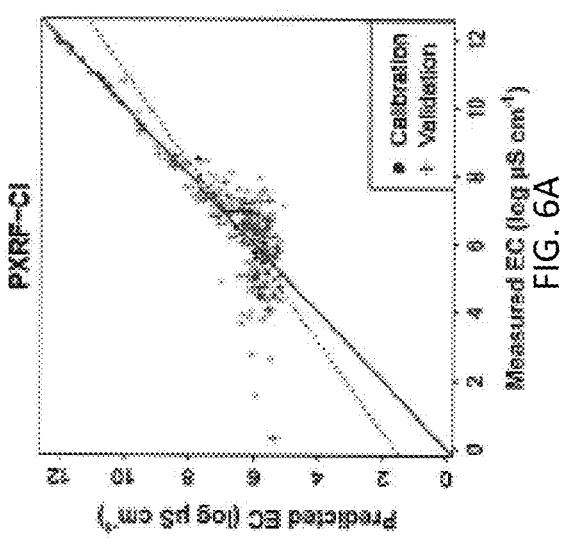
FIGS. 6A-6C are plots of observed vs. model predicted EC values showing both calibration and validation data (with dotted 1: I line)
Figure 6B:
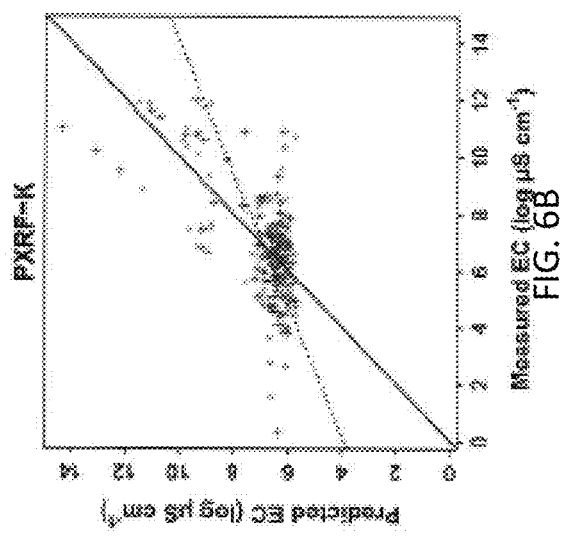
Figure 6C:
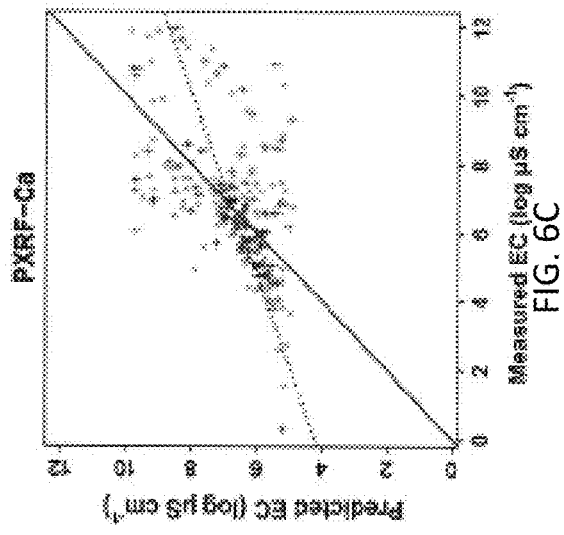

Plots of measured vs. PXRF predicted EC values are presented in FIGS. 6A-6C. In general, all models showed overestimation at lower EC values and underestimation at higher values. Several of these overestimations occurred because of the relative scarcity of observations with low EC values. The equations for all three PLR models are presented in Table 4.

TABLE 4

Water EC calibration model equations (n = 176) using PXRF measured elements as predictors.

| Predictor (log transformed) | Model[a] | Calibration model equation |
|---|---|---|
| PXRF Cl (mg kg$^{-1}$) | PLR | log(EC) = −1.070 + 1.620 * log(PXRF-Cl) − 0.820 * log(PXRF-Cl) * 1[log(PXRF-Cl) > 5.379][b] |
| PXRF K (mg kg$^{-1}$) | PLR | log(EC) = −13.780 + 4.132 * log(PXRF-K) − 2.899 * log(PXRF-K) * 1[log(PXRF-K) > 5.434] |
| PXRF Ca (mg kg$^{-1}$) | PLR | log(EC) = −11.078 + 3.442 * log(PXRF-Ca) − 6.104 * log(PXRF-Ca) * 1[log(PXRF-Ca) > 6.084] |

[a]PLR, piecewise linear regression.
[b]1(x > a) is an indicator function. If x is not greater than a, 1(x > a) = 0, otherwise (i.e. x > a) 1(x > a) = 1.

Figure 7:
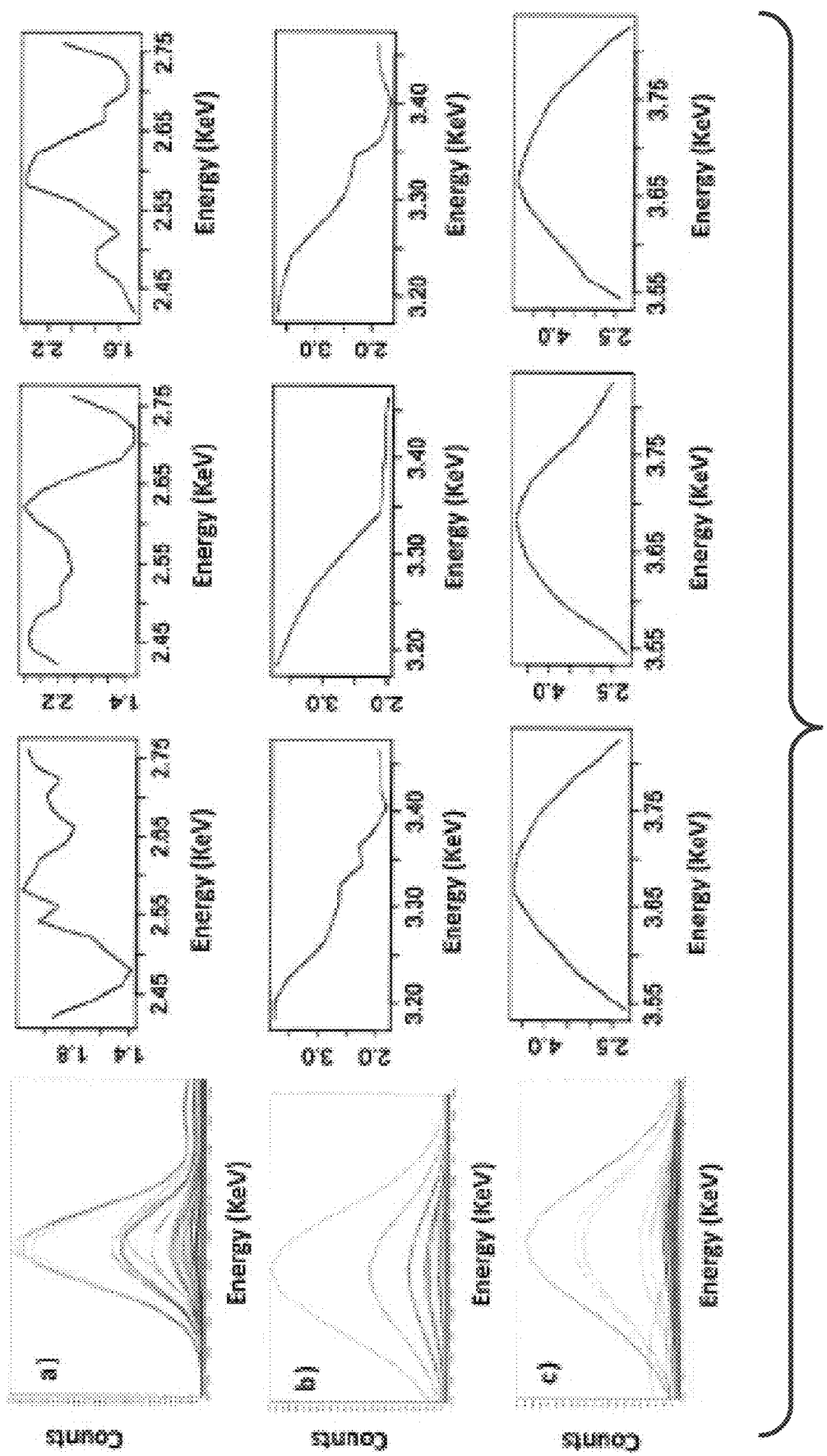
FIG. 7 are stacked non-transformed and selected log-transformed examples of baseline corrected and smoothed XRF emission lines of (a) Cl (2.62 keV), (b) K (3.31 keV) and (c) Ca (3.69 keV)

FIG. 7 represents stacked and some log-transformed isolated examples of baseline corrected and smoothed XRF emission lines of Cl (2.62 keV), K (3.31 keV), and Ca (3.69 keV). Notably, while comparing all three stacked XRF spectra indicating different elemental concentrations of Cl, K, and Ca, most of them could not be distinguished from each other despite wider ranges of elemental concentrations in water samples (Table 2). Without log-transformation, most of the data were actually in the bottom of the plot. For example, in PRXF-K, 95% of the samples had the peak value <253. Note that, on log-transformed PXRF-Cl, Ca, and K spectra, only PXRF-Ca bumps produced FWHM values while most of PXRF-Cl bumps were unable to generate FWHM values due to their multi-modal shape. Besides, most of the PXRF-K bumps were monotonic and thus unsuitable to deduce the FWHM values. Moreover, using $H_{max}$ representing changes in elemental concentrations, no better correlation was obtained than using elemental results (data not shown). Thus, the postulation of Sacristan et al. (2016) that using $H_{max}$ known or FWHM could be a fast and easy quantification method without complex data processing and matrix effects, may not be generalized and warrants more studies to find the suitable spectral preprocessing methods.

The results described herein show that PXRF can be employed for rapid water salinity quantification or at least for screening purposes which require moderate precision. The predictability can be enhanced with increasing variability in Cl concentrations in the water samples. Given these results, PXRF shows an effective approach for rapid, on-site assessment of heavy metals and/or other pollutants in waters, as will be described in another example below. It is widely known that "heavier" elements are more easily quantified by PXRF owing to a larger electron cloud. In soils, limits of detection for such elements can be as low as ~5 mg kg$^{-1}$. Although longer scanning times can be used, the increased accuracy by such extended scanning times must be considered against the alacrity gained by using PXRF. Finally, fine tuning of PXRF fluorescence energy spectra can be undertaken to provide a Water Mode on the PXRF instrument. Such a configuration would intrinsically consider the low density matrix of the water being scanned such that other elemental signatures could be parsed from the fluorescent energy.

Although water salinity assessment via electrical conductivity may be just as easy as the use of PXRF, PXRF provides actual elemental concentration (Cl) which may be useful in identifying certain types of salt(s) dissolved in solution: information not provided by simple electrical conductivity assessment. That notwithstanding, a key novelty of this study is the fact that water samples can be scanned via PXRF with significant statistical relationships to standard laboratory techniques. Based on the inventors' knowledge, this represents the first such study of PXRF assessment of water samples. The use of PXRF for analysis of pollutant and/or metal contaminated waters has been established by protocols presented in the context of the studies described herein.

This present study was a proof of concept demonstration and presented an easy and convenient PXRF protocol for quantifying water EC with Cl, K. and Ca. Results show that combining 2-segmented PLR models with PXRF-Cl produced acceptable prediction accuracy for water EC while no realistic agreements were observed between water EC and PXRF-K and Ca. This was possibly due to matrix effects represented by absorption and secondary fluorescence. The poor EC predictability while using PXRF spectral parameters like FWHM and $H_{max}$ underlies the need for better spectral PXRF preprocessing methods and factory calibration of PXRF to include a Water Mode. However, the results obtained herein point to using PXRF for future rapid analysis of water samples in-situ.

Yet another non-limiting example of using the present invention to determine metal content within a liquid will now be described. A rapid method for in-situ elemental composition analysis of metal-laden water would be indispensable for studying polluted water. Current analytical lab methods to determine water quality include flame atomic absorption spectrometry (FAAS), atomic absorption spectrophotometry (AAS), electrothermal atomic absorption spectrometry (EAAS), and inductively coupled plasma (ICP) spectroscopy. However only two field methods, colorimetry and absorptiometry, exist for elemental analysis of water. Portable X-ray fluorescence (PXRF) spectrometry is an effective method for elemental analysis of soil, sediment, and other matrices. However, the accuracy of PXRF is known to be affected while scanning moisture-laden soil samples. This study sought to statistically establish PXRF's predictive ability for various elements in water at different concentrations relative to inductively coupled plasma atomic emission spectroscopy (ICP-AES). As will be described in more detail below, the PXRF showed differential effectiveness in elemental quantification. For example, the best relationships between ICP and PXRF elemental data for the collected samples were obtained for K and Cu ($R^2$=0.92). However, when scanning ICP calibration solutions with elements in isolation, PXRF results indicated near perfect agreement; Ca, K, Fe, Cu and Pb produced an $R^2$ of 0.99 while Zn and Mn produced an $R^2$ of 1.00. The results of this study demonstrated the PXRF's ability to satisfactorily predict the composition of metal-laden water as reported by ICP for several elements.

Several well-known limitations do exist for PXRF, one of which specifically relates to moisture causing fluorescence attenuation (Weindorf et al., 2014). Further, it is well established that PXRF cannot attain the low limits of detection nor precision offered by ICP or other laboratory-based instrumentation. Contrariwise, PXRF offers speed, portability, and reasonable accuracy that may far surpass current field techniques such as colorimetry. Even if PXRF was able to effectively differentiate remarkable from non-remarkable samples for certain elemental concentrations in solution, it would still remain a formidable advance over current techniques, one which could potentially save both time and money.

Given the rapid advancements of PXRF for chemical analysis in numerous matrices, its evaluation for direct assessment of polluted water seems timely. As such, the objective of this study was to statistically establish PXRF's predictive ability for various elements in water at different concentrations relative to ICP. We hypothesize that PXRF will aptly quantify numerous elements in water at concentrations of 10-10,000 mg $L^{-1}$.

A total of 390 water samples were collected from leaching columns of mine tailings in South Africa. Leaching of the tailings was generally in accordance with Method D5744-13 (ASTM, 2013). With deference and respect to maintaining mine operator anonymity, the exact mines sampled cannot be disclosed. However, they were generally an assortment of Cu, U, Zn, Ag, and Au mines. In addition to common soil mineral matrices (e.g., montmorillonite, biotite, quartz, calcite, hematite, gypsum, muscovite), substantive concentrations of more exotic minerals (e.g., gahnite, sphalerite, galena, nchwaningite, uranopolycrase, billietite, chlorargyrite, cuprospinel) were found (as confirmed by X-ray diffraction) in the tailing samples subjected to leaching.

Prior to leaching, each tailings sample was ground to <6 mm and placed in a column. Each column was leached with 750 ml of deionized water, then preserved with $HNO_3$ and stored in clean, sealed bottles at 4° C. Samples were then transported to Texas Tech University (Lubbock, Tex., USA) for analysis in the Pedology laboratory.

Prior to analysis, samples were allowed to return to room temperature (20° C.). Any samples containing suspended particles were filtered with #2 filter paper (Micro Filtration Systems, Dublin, Calif., USA) before analysis. Each sample was placed in a Series 1400 plastic sample cup (Chemplex Industries, Palm City, Fla., USA), then covered with Prolene® thin-film (Chemplex Industries, Palm City, Fla., USA). A Delta Premium (DP-6000) PXRF (Olympus-Innov-X; Waltham, Mass., USA) was calibrated with a standard 316 metal alloy target prior to scanning the samples. PXRF instrument performance was validated via the scanning of multiple ICP standards. The PXRF was stationed in a proprietary test stand, that shields the user from errant X-rays, and the sample cups were place on the sample stage and inverted directly over aperture of the PXRF. The instrument was set to SoilMode and configured to scan each sample with three 30 s beams, totaling 90 s of scanning per sample (Weindorf and Chakraborty, 2016). Beams one and two were both operated at 40 keV, while beam three was operated at 15 keV. Following scanning, two types of data were downloaded from the instrument: elemental data (as reported by the software as configured), and raw fluorescent energies (spectra) [reported as counts and fluorescent energy (keV) for each scan]. Elemental data is ideal for straightforward applications, while raw spectral data allows for advanced analysis.

All samples underwent inductively coupled plasma optical emission spectroscopy (ICP-OES) analysis with an iCAP7400 model instrument (Thermo Fisher Scientific, Waltham, Mass., USA). High purity argon was used as plasma, auxiliary, and nebulizer gas. The data acquisition integration and wash times were 30 s, with 3-time repetition, and averaged over the three (Bettinelli et al., 2000). The calibration standards were custom ICP standards 1, 2, 3, 4, and 5 (SCP Science, Montreal, QC, Canada), each diluted to six levels (L1 through L6). Check calibration standards (L2 and L4) were inserted after every 50 samples to check consistency.

To improve the capability to fit models and test their results, the elements with <10% missing data (non-detected) were retained by replacing the non-detected values with half of its corresponding PXRF limit of detection (LOD). Simple linear regression (SLR) was used to correlate between the PXRF elemental data and ICP measured elements in water samples using R 2.11.0 (R Development Core Team, 2014). For individual elements, the whole dataset was randomly split into 70% calibration and 30% validation sets. Further SLR modeling was executed for predicting elements in the ICP calibration standards using PXRF elemental data.

To eliminate the artifacts arising from the PXRF device or sample geometry, XRF spectra were preprocessed using the Unscrambler 10.4x (CAMO Software Inc., Woodbridge, N.J., USA) software. As thus far, there is no generally established method for the preprocessing of PXRF spectra, the method proposed by O'Rourke et al. (2016) was followed with some modifications. The DP-6000 PXRF covers all contaminant metals with optimized three-beam kV-filter-current settings where an individual beam is optimized for a suite of metals. For one set of analysis and instead of selecting all three bands from Soil Mode, individual fluorescence beams from Soil Mode were extracted as follows:

Fe (beam two), Zn (beam two), Ca (beam three), Cu (beam two), Mn (beam three) and K (beam three). For additional analysis and comparison to previous approaches (O'Rourke et al., 2016), the three fluorescence beams of Soil Mode were stacked to exploit the advantage of longer scanning time. Single beam fluorescence spectra evaluation was baseline corrected and a second-order Savitzky-Golay (SG) smoothing algorithm with a span length of three points was used to smooth each spectrum by optimizing the signal to noise ratio (Savitzky and Golay, 1964). No such pre-treatment was applied to the stacked (three beam) approach. The full PXRF spectra were calibrated with the analyte of interest using partial least squares regression (PLSR) since it is the most widely used multivariate method. Based on spectral variance, PLSR extracts latent factors and subsequently correlates them with the component of interest. In this study, PLSR models with 30% independent validation were developed via R 2.11.0 to explore the correlation between PXRF spectra and both ICP and PXRF elemental data.

Model assessment for both SLR and PLSR was accomplished using root mean squared error (RMSE), residual prediction deviation (RPD), the coefficient of determination ($R^2$) and the ratio of performance to interquartile range (RPIQ) (Chakraborty et al., 2017a,b) per Eqs. 1-3:

$$R^2 = 1 - \frac{\sum_{i=1}^{n}(Y_i - \hat{Y}_i)^2}{\sum_{i=1}^{n}(Y_i - \overline{Y}_i)^2} \quad (1)$$

$$RMSE = \sqrt{\sum_{i=1}^{n}\left[\frac{(\hat{Y}_i - Y_i)^2}{n}\right]} \quad (2)$$

$$RPD = \left[\frac{1/(n-1)\sum_{i=1}^{n}(Y_i - \overline{Y}_i)^2}{1/n\sum_{i=1}^{n}(Y_i - \hat{Y}_i)^2}\right]^{0.5}_{Validation} \quad (3)$$

where, $Y_i$, $\hat{Y}_i$, $\overline{Y}_i$ and n denote observed target variable, predicted target variable, mean of the target variable and sample number, respectively. Notably, RPIQ is an indicator of the goodness of the calibration models and was calculated as the interquartile range IQ/RMSE of prediction per Eq. 4:

$$IQ = Q3 - Q1 \quad (4)$$

where, Q3 and Q1 are the third and first quartile, respectively.

The extracted baseline corrected and smoothed PXRF spectra for individual element were further preprocessed to extract Kα emission lines of Fe (6.40 keV), Zn (8.63 keV), Ca (3.69 keV), Cu (8.04 keV), Mn (5.89 keV) and K (3.31 keV). For each individual extracted peak, full width at half maximum (FWHM) and the maximum height ($H_{max}$) were extracted per Sacristan et al. (2016). The peak parameters were extracted using Originpro (OriginLab, MA, USA) and subsequently used to predict both PXRF and ICP reported elemental concentrations.

Figure 8:
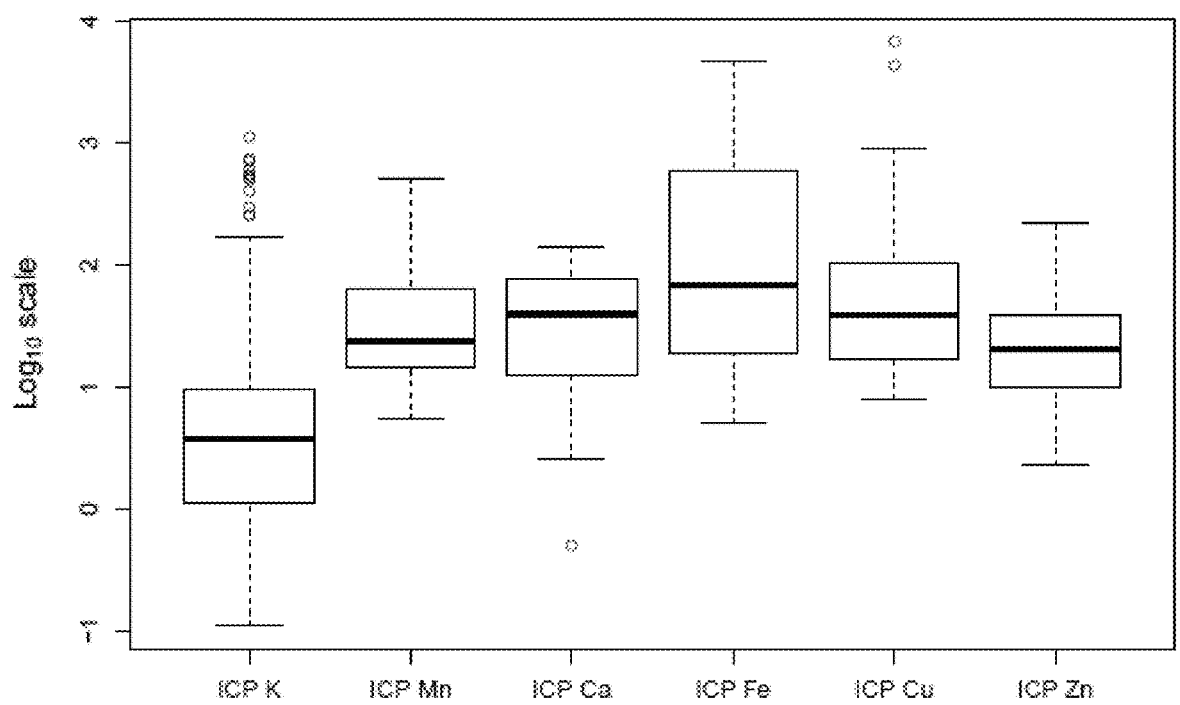
FIG. 8 are box and whisker plots showing elemental concentrations in water samples as derived from ICP analysis.
Figure 9:
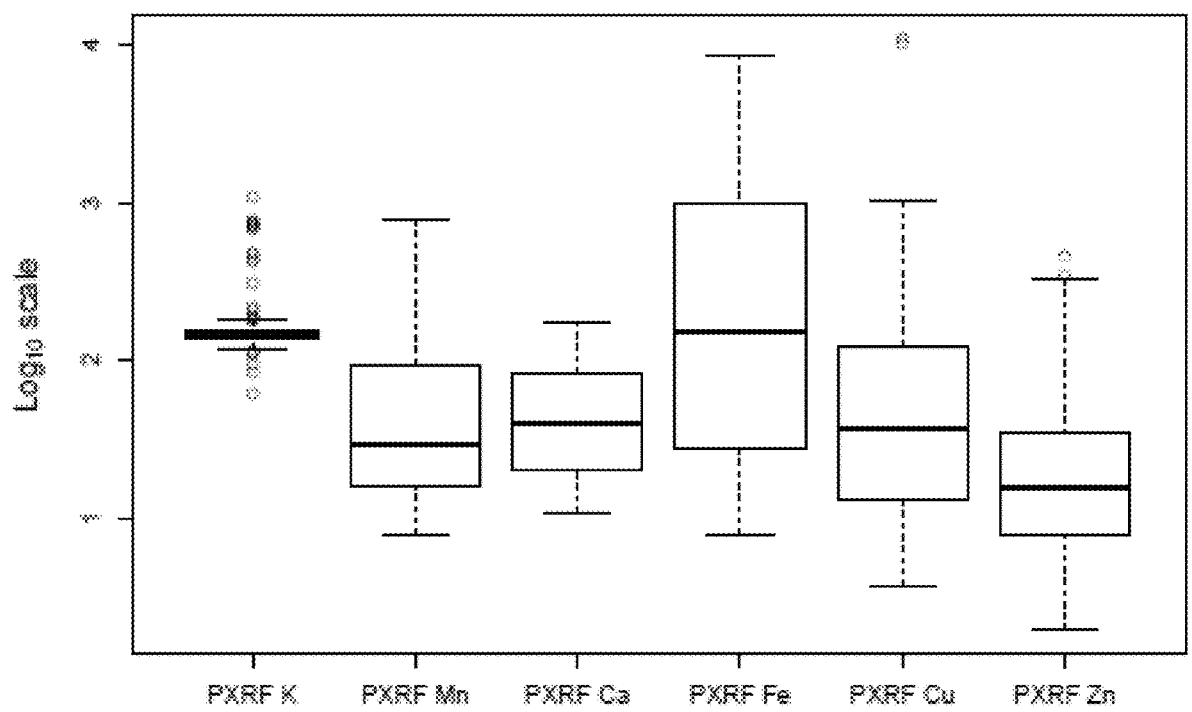
FIG. 9 are box and whisker plots showing elemental concentrations in water samples as derived from PXRF scanning.

Table 5 represents summary statistics of ICP and PXRF measured elements in water samples. Additionally, FIGS. 8 and 9 exhibit box and whisker plots showing ICP and PXRF elemental data, respectively. As anticipated, results showed substantial variation in elemental concentrations in water samples as measured by both ICP and PXRF (Table 5, FIGS. 8 and 9), indirectly implying the inherent geochemical diversity of the mine tailings. For instance, among ICP reported elements Fe (4,684.9 mg kg$^{-1}$) and Cu (6,699.0 mg kg$^{-1}$) exhibited almost five and seven folds wider ranges than K (1,096.8 mg kg$^{-1}$) (Table 5). For comparison, Barreiros et al. (1997) reported the maximum allowed values for drinking water as follows (all in μg L$^{-1}$): K 12,000; Cr 50; Mn 50; Fe 200; Ni 50; As 50; Se 10; Cd 5; Sb 10; Hg 1; Pb 10. Conversely, Ca content varied from 0 to 137.5 mg kg$^{-1}$. Following a similar trend, PXRF reported Fe (8,550.0 mg kg$^{-1}$) and Cu (10,706.2 mg kg$^{-1}$) exhibited ~8.5 and 10 folds wider ranges than K (1,034.0 mg kg$^{-1}$). For Mn, Ca, and Zn both PXRF and ICP reported relatively close mean elemental concentrations, yielding a reasonable agreement. Nevertheless, for Fe and Cu PXRF reported ~1.5 folds higher mean elemental concentration than ICP. Contrariwise, PXRF K showed more than fivefold higher mean content (161.4 mg kg$^{-1}$) than the average ICP K (23.6 mg kg$^{-1}$). Notably, the inherent chemical complexity of mine tailing water was also reported by several researchers (Simon et al., 1999; Moncur et al., 2015). In this study, ICP and PXRF reported mean Fe concentration was 499.5 and 794.9 mg kg$^{-1}$, respectively; signifying marked enrichment of iron oxides in analyzed water samples. Indeed, low temperature mine waters are usually supersaturated with goethite along with other Fe-oxyhyroxides (Moncur et al., 2015). Notably, substantive concentrations of Fe were present in the mine tailings used to produce the leachate tested, among them hematite, magnetite, and magnesioferrite. Pearson et al. (2017) concluded that the difference between ICP and PXRF based results was perhaps due to the Soil Mode calibration of PXRF, inherently targeted for a soil matrix and associated matrix density. Soil particle densities are dependent upon mineralogy, with one of the most common being 2.65 g cm$^{-3}$, that of quartz (Weil and Brady, 2017). Yet certain minerals feature considerably higher particle densities (e.g., magnetite 5.15 g cm$^{-3}$; hematite, 5.30 g cm$^{-3}$; pyrite 5.01 g cm$^{-3}$). Another possible reason could be the disproportionate self-absorption resulting from excessive elemental enrichment in water samples. These results indicated the necessity of developing water matrix specific PXRF calibrations.

TABLE 5

Summary statistics of ICP and PXRF measured elements in water samples.

| Element | Observations | Min | Max | Range | 1st Quartile | Median | 3rd Quartile | Mean | Standard deviation |
|---|---|---|---|---|---|---|---|---|---|
| ICP measured elements | | | | | | | | | |
| K (mg kg$^{-1}$) | 386 | 0.11 | 1096.9 | 1096.8 | 1.1 | 3.7 | 9.4 | 23.6 | 101.2 |
| Mn (mg kg$^{-1}$) | 386 | 5.38 | 509.2 | 502.8 | 14.6 | 23.4 | 64.0 | 70.6 | 106.2 |
| Ca (mg kg$^{-1}$) | 336 | 0.00 | 137.5 | 137.5 | 12.3 | 39.2 | 77.4 | 47.3 | 37.9 |

TABLE 5-continued

Summary statistics of ICP and PXRF measured elements in water samples.

| Element | Observations | Min | Max | Range | 1st Quartile | Median | 3rd Quartile | Mean | Standard deviation |
|---|---|---|---|---|---|---|---|---|---|
| Fe (mg kg$^{-1}$) | 386 | 4.95 | 4689.8 | 4684.9 | 18.9 | 68.8 | 586.7 | 499.5 | 879.1 |
| Cu (mg kg$^{-1}$) | 386 | 7.88 | 6706.9 | 6699.0 | 17.2 | 39.0 | 99.1 | 237.3 | 1035.9 |
| Zn (mg kg$^{-1}$) | 386 | 2.28 | 215.2 | 212.9 | 9.9 | 20.1 | 38.1 | 34.6 | 41.1 |
| PXRF measured elements | | | | | | | | | |
| K (mg kg$^{-1}$) | 386 | 62.0 | 1096.0 | 1034.0 | 137.0 | 145.0 | 153.0 | 161.4 | 96.9 |
| Mn (mg kg$^{-1}$) | 386 | 8.0 | 774.0 | 706.0 | 16.0 | 30.0 | 95.0 | 113.4 | 176.5 |
| Ca (mg kg$^{-1}$) | 386 | 11.0 | 177.0 | 166.0 | 20.0 | 41.0 | 82.0 | 55.0 | 40.7 |
| Fe (mg kg$^{-1}$) | 386 | 8.0 | 8558.0 | 8550.0 | 28.0 | 153.0 | 1003.0 | 794.0 | 1514.0 |
| Cu (mg kg$^{-1}$) | 386 | 3.8 | 10710.0 | 10706.2 | 13.4 | 37.9 | 120.5 | 468.9 | 1892.2 |
| Zn (mg kg$^{-1}$) | 386 | 2.0 | 453.0 | 451.0 | 7.80 | 35.9 | 34.9 | 51.9 | 93.5 |

Figure 10:
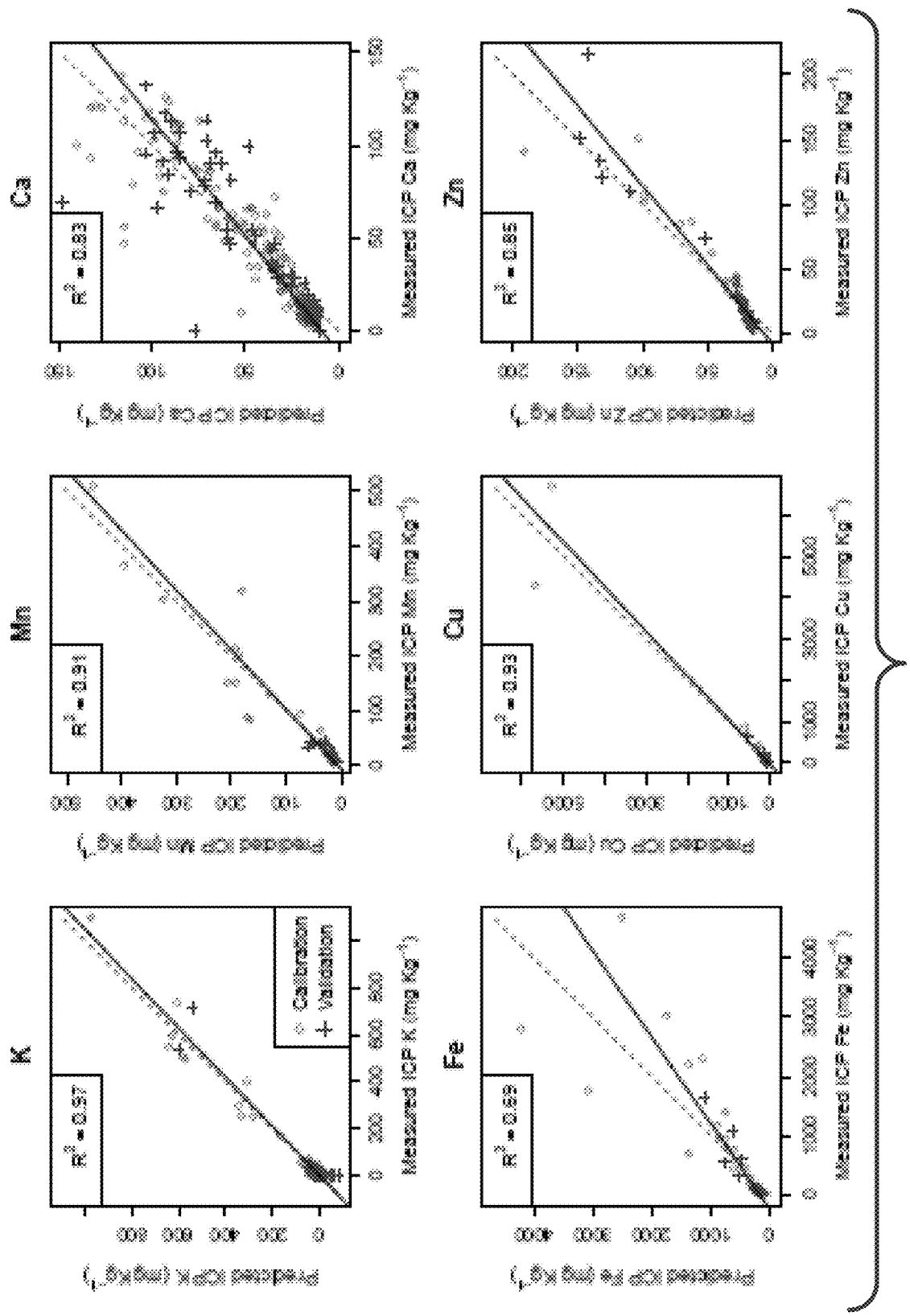
FIG. 10 are plots showing PXRF predicted ICP elements vs. measured ICP elements in water samples.
Figure 11:
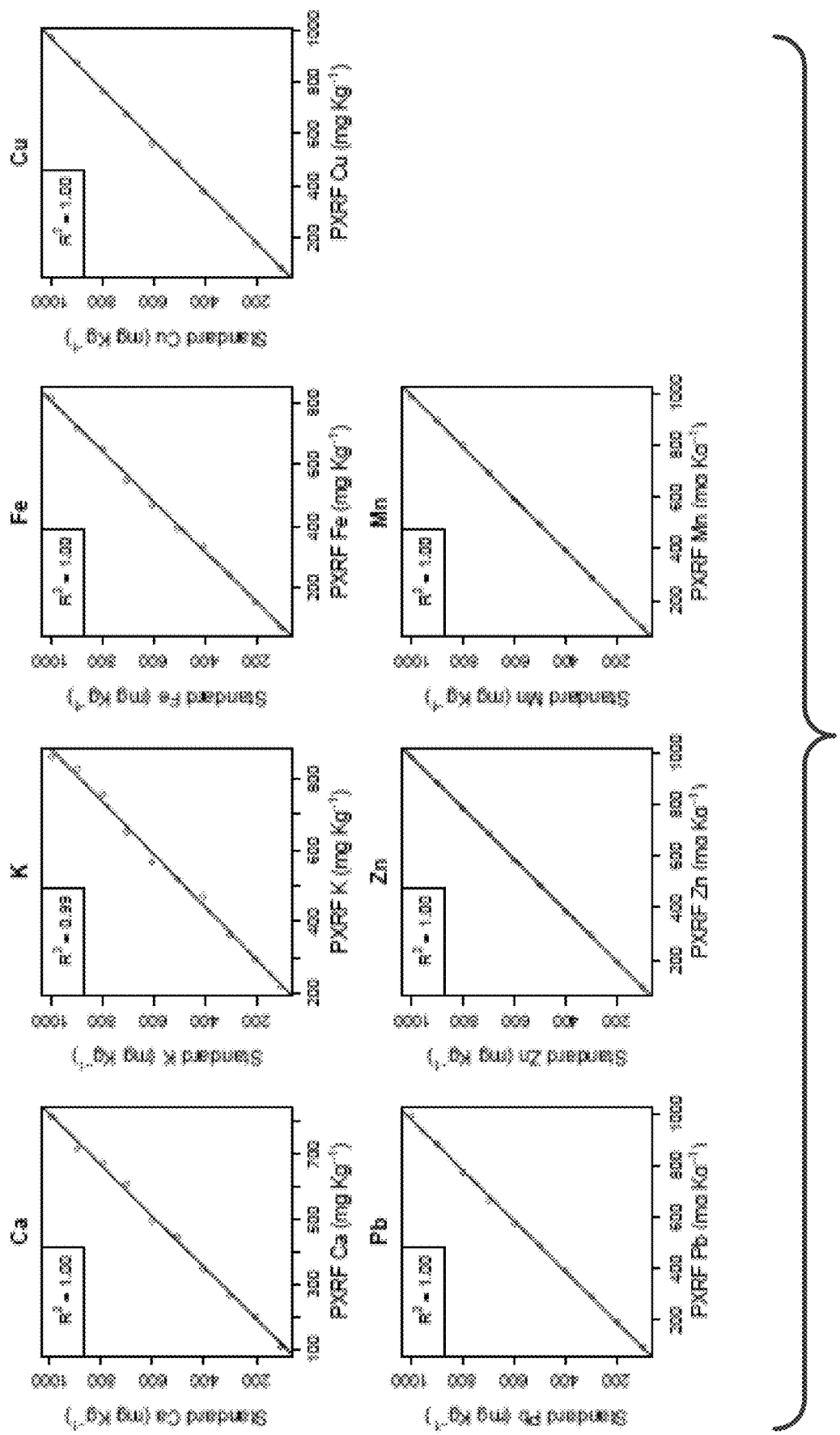
FIG. 11 are plots showing ICP calibration standards via PXRF elemental data.

Given the accuracy of PXRF for predicting mine tailings (Koch et al., 2017) and water electrical conductivity (Pearson et al., 2017), SLR models were applied to predict the ICP-based elemental composition of water samples using PXRF elemental data as inputs. Models yielded calibration $R^2$ ranging from 0.69 to 0.97, suggesting that ICP reported elements in water can be satisfactorily predicted by the corresponding PXRF elemental data (Table 6). PXRF predicted ICP elements vs. measured ICP elements are shown in FIG. 10. It was apparent that except for Ca, the remaining elements showed different degrees of underestimation at higher analyte values, possibly due to a lack of samples with higher ends of the property scale. The highest calibration $R^2$ was reported for K (0.97) with an RMSE of 19.35 mg kg$^{-1}$. Notably, as per Chang et al. (2001) proposed RPD-based guidelines, all calibration models exhibited accurate results with RPD values >2 (Table 6). These results were maintained in validation sets except for Mn where validation $R^2$ was suboptimal (0.51), indicating an overfitted calibration algorithm. The best correlation between ICP elemental data and PXRF elemental data in the validation sets were obtained for K and Cu ($R^2$=0.92). Further, the best RPIQ values for both calibration set (3.54) and validation set (3.48) were produced by Ca. While predicting the ICP calibration standards via PXRF measured elements, results indicated almost perfect agreements where five (Ca, K, Fe, Cu and Pb) out of seven tested elements produced an identical $R^2$ of 0.99 and the remaining two elements (Zn and Mn) produced a perfect $R^2$ of 1.00 (Table 7, FIG. 11). Interestingly, despite the ability of PXRF to perfectly predict Mn in ICP calibration standards, the poor validation results obtained while predicting ICP based Mn values may be ascribed to the limitation of the random data splitting scheme (Table 6). As postulated by Koch et al. (2017), the inclusion of target variability in the data partitioning procedure might improve the distribution of calibration and validation sets, eventually augmenting the robustness and predictability of the regression model.

TABLE 6

Simple linear regression model results for predicting ICP elements via PXFR elements.

| | Calibration | | | | Validation | | | |
|---|---|---|---|---|---|---|---|---|
| Element | $R^2$ | RMSE[a] | RPD[b] | RPIQ[c] | $R^2$ | RMSE | RPD | RPIQ |
| K (mg kg$^{-1}$) | 0.97 | 19.35 | 5.60 | 0.43 | 0.92 | 22.82 | 3.59 | 0.29 |
| Mn (mg kg$^{-1}$) | 0.91 | 35.77 | 3.43 | 2.96 | 0.51 | 8.93 | 1.48 | 2.78 |
| Ca (mg kg$^{-1}$) | 0.83 | 15.63 | 2.43 | 3.54 | 0.71 | 20.45 | 1.86 | 3.48 |
| Fe (mg kg$^{-1}$) | 0.69 | 553.85 | 1.81 | 1.33 | 0.76 | 206.04 | 2.11 | 1.66 |
| Cu (mg kg$^{-1}$) | 0.93 | 318.64 | 3.89 | 0.27 | 0.92 | 40.30 | 3.59 | 1.47 |
| Zn (mg kg$^{-1}$) | 0.85 | 12.50 | 2.56 | 2.26 | 0.91 | 16.26 | 3.48 | 1.11 |

[a]RMSE, root mean squared error
[b]RPD, residual prediction deviation
[c]RPIQ, ratio of performance to interquartile range

TABLE 7

Simple linear regression model parameters for predicting elements in the ICP calibration standards using PXRF elemental data.

| Element | $R^2$ | RMSE[a] | Intercept | Slope |
|---|---|---|---|---|
| Ca (mg kg$^{-1}$) | 1.00 | 17.57 | −45.96 | 1.26 |
| K (mg kg$^{-1}$) | 0.99 | 22.60 | −198.64 | 1.35 |
| Fe (mg kg$^{-1}$) | 1.00 | 11.99 | 7.99 | 1.22 |
| Cu (mg kg$^{-1}$) | 1.00 | 7.71 | 12.54 | 1.01 |
| Pb (mg kg$^{-1}$) | 1.00 | 8.04 | 2.43 | 1.01 |
| Zn (mg kg$^{-1}$) | 1.00 | 3.03 | 5.73 | 1.01 |
| Mn (mg kg$^{-1}$) | 1.00 | 4.60 | 5.90 | 1.01 |

[a]RMSE, root mean squared error

Figure 12:
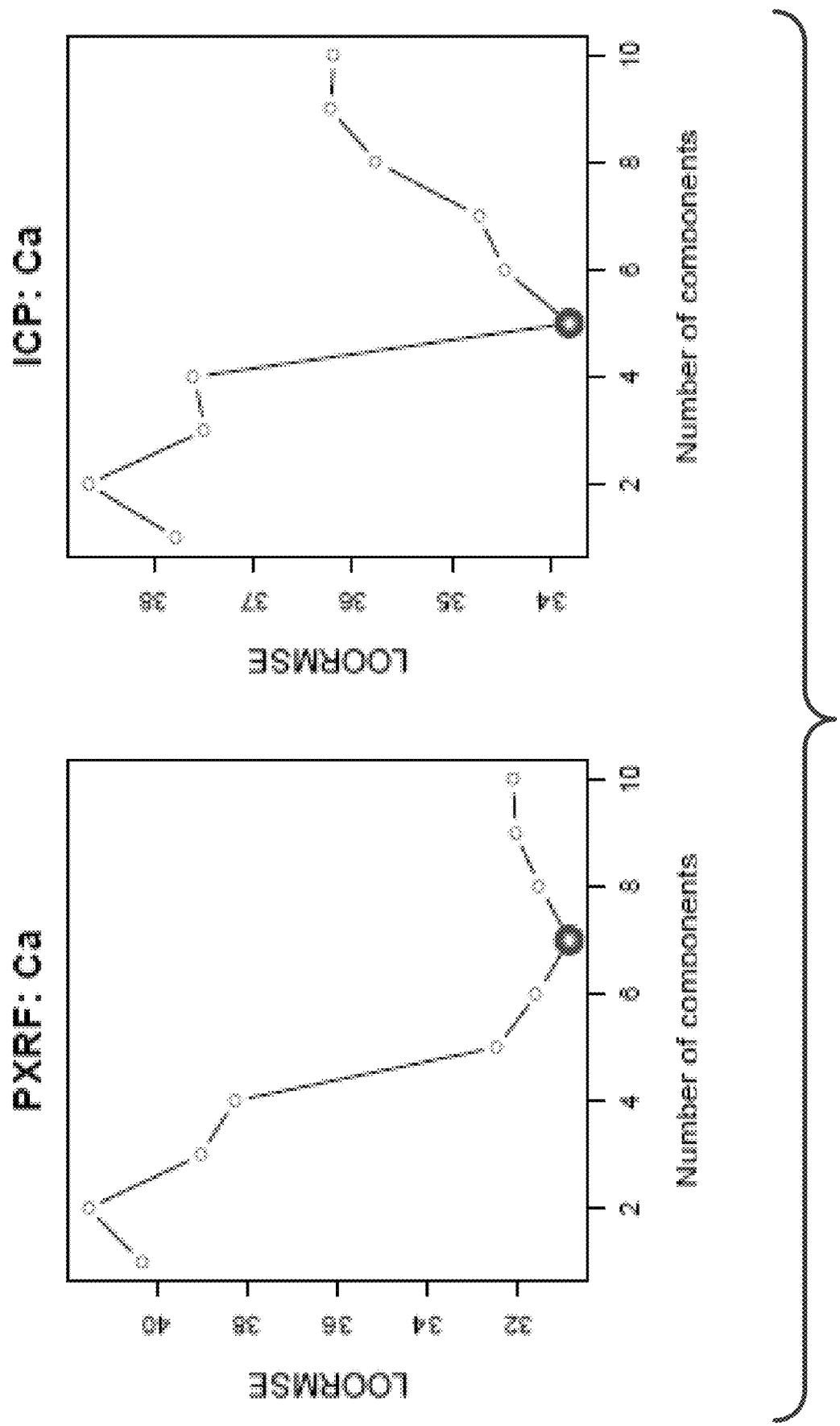
FIG. 12 are plots showing an illustrative example of model selection with optimum PLSR latent factors for both ICP and PXRF measured Ca.

The ability of pretreated whole XRF spectra to predict ICP and PXRF reported elements was a major focus of this study. Plots in FIG. 12 represent an illustrative example of model selection with the optimum number of latent factors for PLSR models which were used for predicting ICP and PXRF reported Ca values via pretreated whole PXRF spectra. Notably, the factor which produces the lowest leave-one-out-cross-validation RMSE is generally considered as the optimum. While calibrating the ICP reported elements using full pretreated XRF spectra, PLSR produced satisfactory calibration $R^2$ for all elements except for Cu (0.61) (Table 8). Among all the tested elements, the highest model generalization was achieved for Mn ($R^2$=0.97, RMSE=17.92 mg kg$^{-1}$) followed by Fe ($R^2$=0.93, RMSE=216.65 mg kg$^{-1}$) and Zn ($R^2$=0.92, RMSE=11.48 mg kg$^{-1}$). These three elements also performed satisfactorily while validating with 30% independently drawn test set. Notably, the highest validation RPD was produced by Fe (3.18) followed by Mn (2.00). Nevertheless, validations results worsened for Ca, Cu, and K, producing $R^2$ values of <0.30. The results converged with the findings of O'Rourke at al. (2016), although they targeted soil elements instead of water. However, O'Rourke et al. (2016) stacked their fluorescence beams to capitalize on the benefits of extended scanning times. Thus, a single beam approach was compared to a multi-beam approach and an increase in model performance was found with the latter (Table 9). However, users should carefully consider the balance between required analytical accuracy versus optimized sample throughput. For example, single beam quantification produced reasonable validation model accuracy suitable for the determination of several elements (e.g., Fe $R^2$ 0.90; Mn $R^2$ 0.74; Zn $R^2$ 0.60), though in one third the time per sample of the multi-beam approach.

Figure 13:
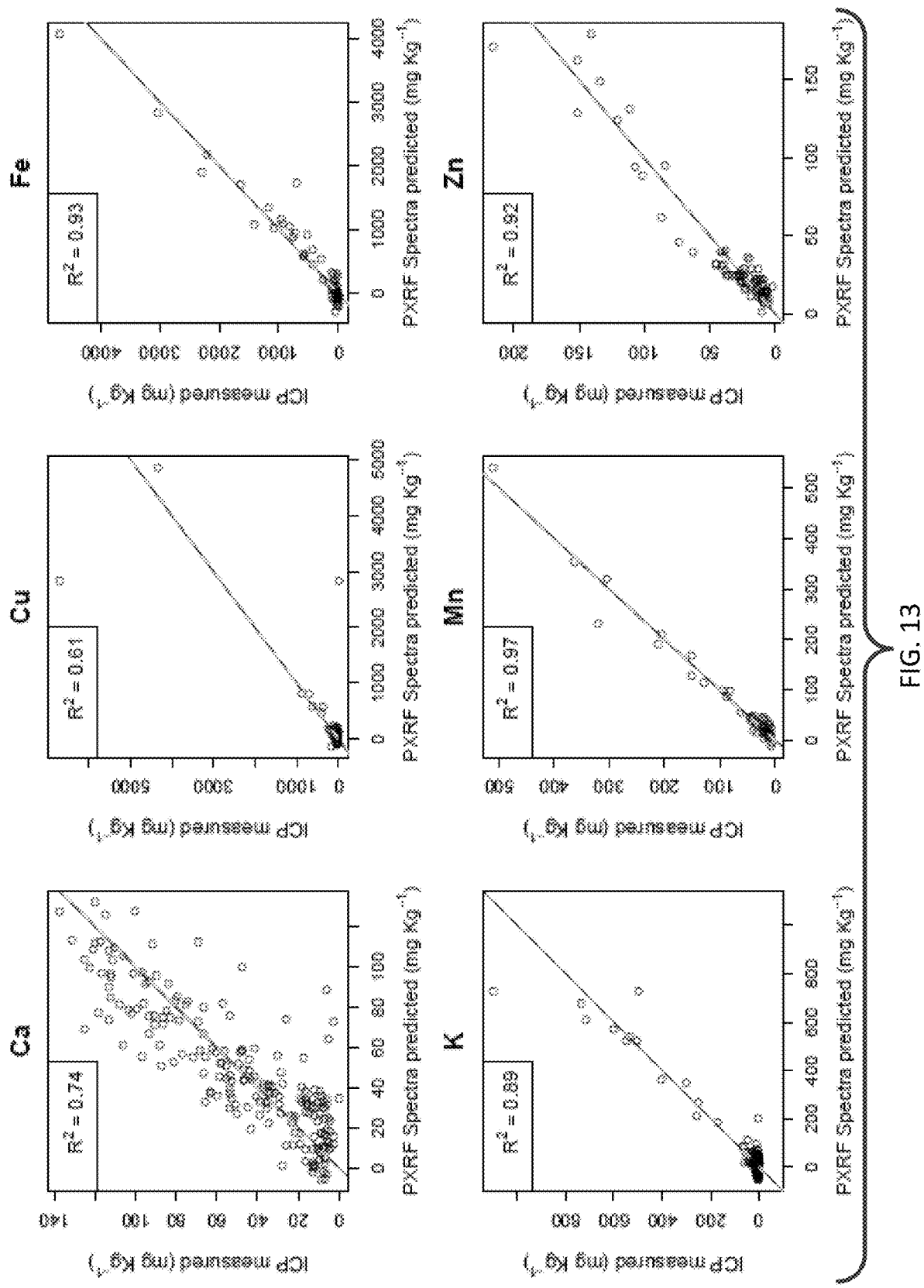
FIG. 13 are plots showing ICP elemental data vs. PXRF spectra predicted ICP data using PLSR algorithm.
Figure 14:
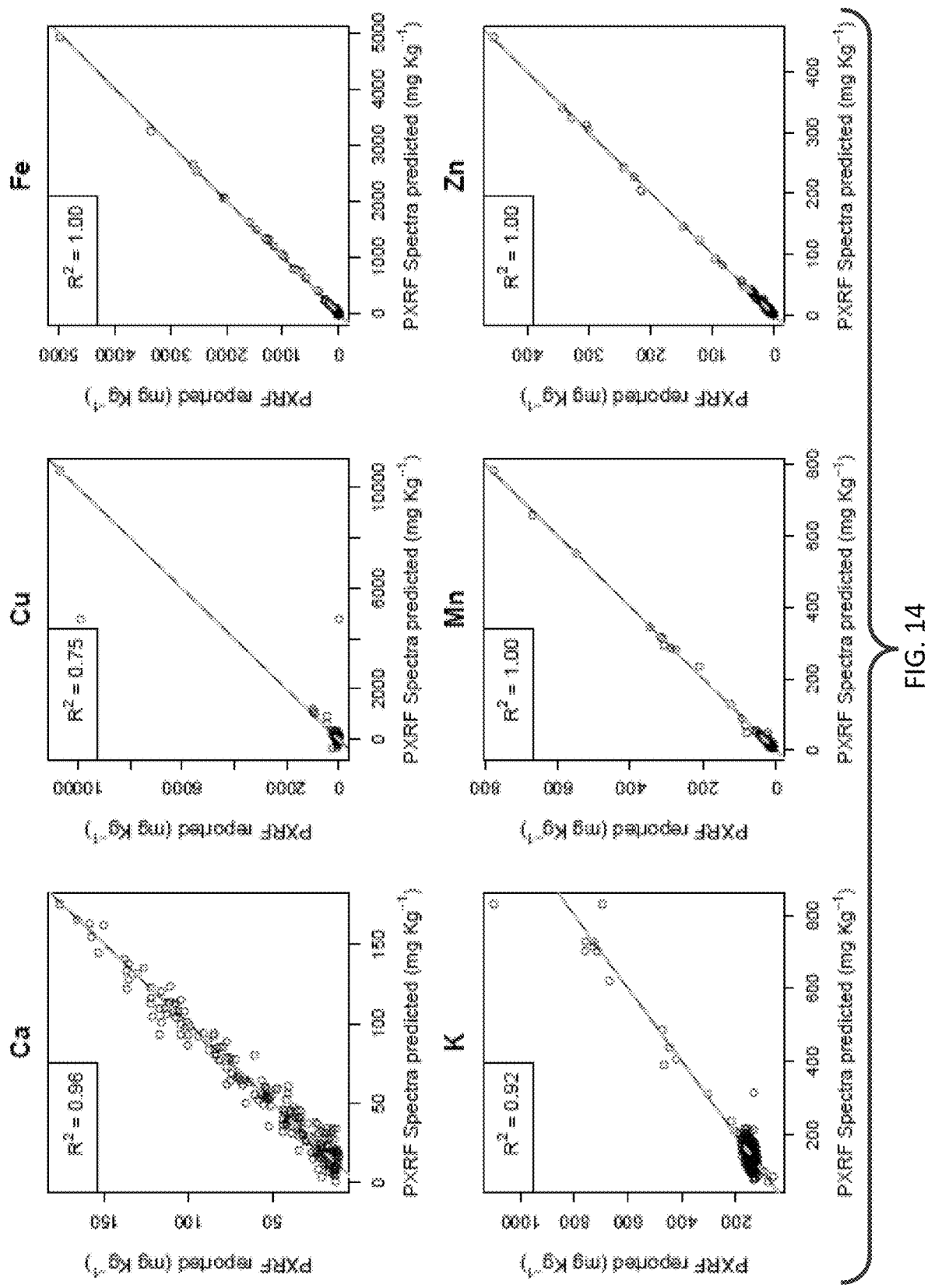
FIG. 14 are plots showing ICP elemental data vs. PXRF spectra predicted elemental data using PLSR algorithm.

Similar trends were followed in the case of PXRF sensed elements where pretreated XRF spectra produced almost perfect calibration results with $R^2$ values ranging from 0.92 to 0.99 for all the elements except for Cu (0.75). While considering the independent validation, the PLSR model of Cu underperformed with an $R^2$ value of 0.33. Plots of both ICP measured and PXRF measured vs. PXRF spectra predicted elements are presented in FIGS. 13 and 14, respectively.

TABLE 8

Partial least squares regression results for predicting ICP elements and PXRF elements via pretreated XRF spectra.

| Element | LP[a] | Calibration | | | | Validation | | | |
|---|---|---|---|---|---|---|---|---|---|
| | | $R^2$ | RMSE[b] | RPD[c] | RPIQ[d] | $R^2$ | RMSE | RPD | RPIQ |
| ICP elements | | | | | | | | | |
| Ca (mg kg$^{-1}$) | 3 | 0.74 | 19.44 | 1.95 | 3.36 | 0.26 | 35.09 | 1.16 | 1.77 |
| Cu (mg kg$^{-1}$) | 6 | 0.63 | 638.06 | 1.62 | 0.12 | 0.27 | 1601.63 | 1.18 | 0.06 |
| Fe (mg kg$^{-1}$) | 3 | 0.93 | 216.68 | 3.81 | 2.61 | 0.90 | 296.27 | 3.18 | 2.89 |
| K (mg kg$^{-1}$) | 10 | 0.89 | 33.16 | 3.05 | 0.24 | 0.10 | 149.59 | 0.65 | 0.11 |
| Mn (mg kg$^{-1}$) | 5 | 0.97 | 17.92 | 5.92 | 2.75 | 0.74 | 88.32 | 2.00 | 0.89 |
| Zn (mg kg$^{-1}$) | 3 | 0.92 | 11.48 | 3.58 | 2.45 | 0.60 | 57.42 | 1.60 | 0.44 |
| PXRF elements | | | | | | | | | |
| Ca (mg kg$^{-1}$) | 7 | 0.96 | 7.78 | 5.23 | 7.99 | 0.43 | 30.54 | 1.32 | 2.01 |
| Cu (mg kg$^{-1}$) | 6 | 0.75 | 936.76 | 2.01 | 0.11 | 0.33 | 1535.04 | 1.23 | 0.06 |
| Fe (mg kg$^{-1}$) | 2 | 0.99 | 30.18 | 31.16 | 28.32 | 0.98 | 101.22 | 9.29 | 8.44 |
| K (mg kg$^{-1}$) | 10 | 0.92 | 28.12 | 3.44 | 0.56 | 0.68 | 54.58 | 1.78 | 0.29 |
| Mn (mg kg$^{-1}$) | 7 | 0.99 | 8.83 | 20.67 | 9.25 | 0.99 | 12.34 | 14.30 | 6.40 |
| Zn (mg kg$^{-1}$) | 5 | 0.99 | 3.08 | 29.73 | 8.82 | 0.99 | 5.77 | 15.84 | 4.70 |

[a]LP, PLS latent factor
[b]RMSE, root mean squared error
[c]RPD, residual prediction deviation
[d]RPIQ, ratio of performance to interquartile range

TABLE 9

Partial least squares regression results for predicting ICP elements via three beams non-pretreated XRF spectra.

| Element | Calibration | | | | Validation | | | |
|---|---|---|---|---|---|---|---|---|
| | $R^2$ | RMSE[a] | RPD[b] | RPIQ[c] | $R^2$ | RMSE | RPD | RPIQ |
| Ca (mg kg$^{-1}$) | 1.00 | 0.005 | 31683.00 | 34231.00 | 0.90 | 83.31 | 3.26 | 1.62 |
| Cu (mg kg$^{-1}$) | 1.00 | 0.007 | 286211.00 | 11577.44 | 0.70 | 124.16 | 1.89 | 1.21 |
| Fe (mg kg$^{-1}$) | 1.00 | 0.13 | 16860.9 | 7191.66 | 0.99 | 924.92 | 17.18 | 3.59 |
| K (mg kg$^{-1}$) | 0.95 | 15.05 | 4.73 | 1.06 | 0.82 | 57.33 | 2.41 | 0.28 |
| Mn (mg kg$^{-1}$) | 1.00 | 0.98 | 198.22 | 100.17 | 0.99 | 10.03 | 12.57 | 2.84 |
| Zn (mg kg$^{-1}$) | 0.99 | 8.53 | 22.27 | 3.27 | 0.99 | 9.51 | 24.67 | 2.54 |

Figure 15:
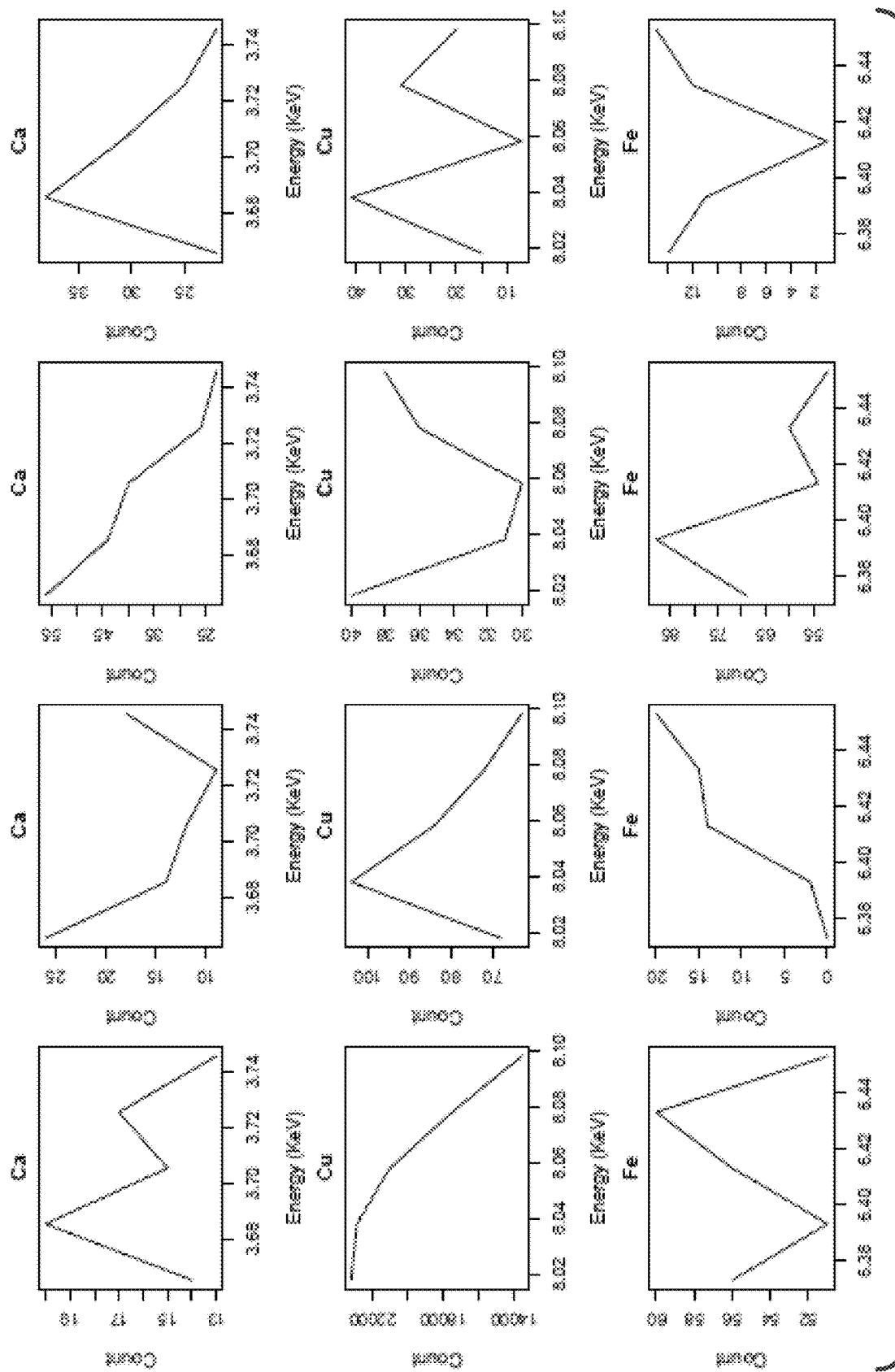
FIG. 15 are typical sample plots for baseline corrected and smoothed PXRF peaks for individual elements.
Figure 15:
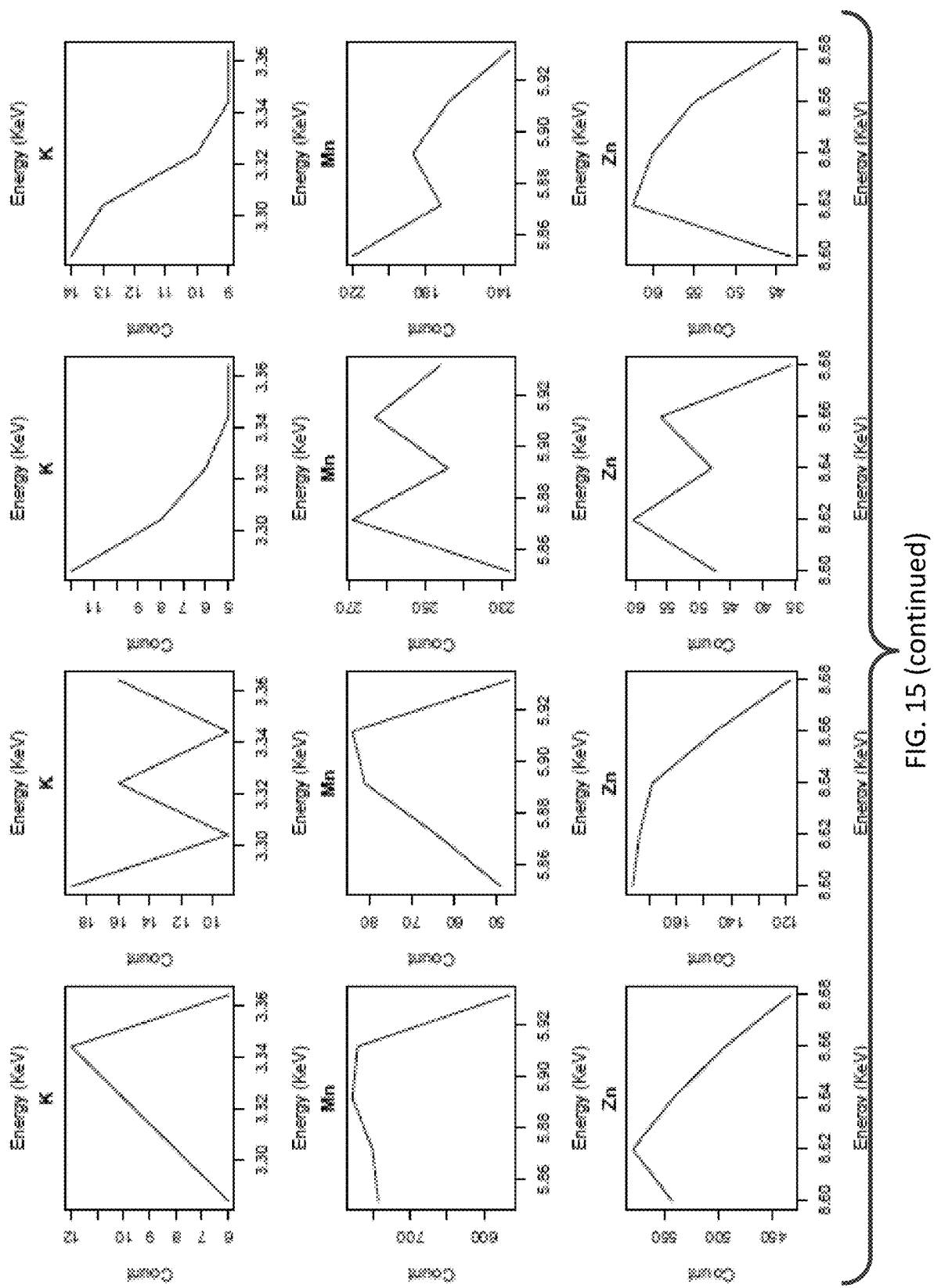

[a]RMSE, root mean squared error
[b]RPD, residual prediction deviation
[c]RPIQ, ratio of performance to interquartile range FIG. 15 shows some typical sample plots for baseline corrected and smoothed PXRF peaks for several individual elements. From the sample curves, some samples exhibited a monotonic relationship between the counts and XRF energy while some plots were bimodal. Besides, some plots showed a U-shaped pattern or zig-zag relationship. All these made it difficult to find the FWHM and $H_m$, which is only possible if the bump has a unimodal shape. However, in the data, the relationship between the counts and energy was more complicated and diversified. For example, only 10 samples for Ca were able to generate FWHH values. These results further validated the findings of Pearson et al. (2017) where the generation of FWHM values for K and Cl peaks was not possible due to their multimodal and monotonic nature. Indeed, it is also imperative to consider interferences between elements in XRF spectra when explaining the PXRF results (Gazley and Fisher, 2014). Consequently, the conclusion of Sacristan et al. (2016) that complex data processing and possible matrix effects in PXRF measurements can be offset easily and rapidly by the exploitation of FWHM and $H_{max}$ warrants further validations.

Summarily, this study confirmed the use of PXRF for quick and on-site elemental characterization of metal-laden water, supplementing conventional standard analyses like ICP. In any case, this approach can be used for rapid screening of water quality which demands modest precision; substantively better precision that simply colorimetry or other field based tests. It can be concluded that the predictability of certain elements can be further enhanced by increasing the variability of analyte concentrations in water samples. Some researchers may argue that the prediction accuracy can be increased by increasing the PXRF scanning time. Yet, the enhanced PXRF predictability by such increased scanning time has to be taken into account against the speed achieved by using PXRF. Most importantly, this research has underlined the necessity of a Water Mode calibration for the PXRF instrument for the better management of XRF spectra in a low-density water matrix.

This study presented a proof of concept demonstration and proposed a simple and convenient procedure for predicting the elemental composition of metal-laden water. Results indicated that water elemental contents as reported by standard ICP based protocol can be satisfactorily predicted by the corresponding PXRF measured elements. As expected, for many elements ICP had the lowest limit of detection, but PXRF provided wide dynamic range of quantification (e.g., <10 to >1,000 mg $kg^{-1}$) with no need for dilutions or sample preparation. PXRF scanning of individual elements isolated in ICP standards produced robust results for each element evaluated ($R^2$ of 0.99 to 1.00), while validation ICP/PXRF statistics for collected water samples showed a strong $R^2$ for K (0.92), Cu (0.92), and Zn (0.91). Besides, pretreated whole XRF spectra were able to predict both ICP and PXRF reported elements via PLSR algorithm. However, utilization of all three spectral beams produced stronger results than use of a single beam in isolation. This research also underlined the necessity of a Water Mode calibration for a low-density water matrix and better spectral preprocessing methods than the use of extracted FWHH and $H_{max}$ values.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

All of the systems, devices, computer programs, compositions and/or methods disclosed and claimed herein can be made and executed without undue experimentation in light of the present disclosure. While the systems, devices, computer programs, compositions and methods of this invention have been described in terms of preferred embodiments, it will be apparent to those of skill in the art that variations may be applied to the systems, devices, computer programs, compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Akaike, H., 1973. Information theory and the extension of the maximum likelihood principle. In: Petrov, V. N., Csaki, F. (Eds.), 2nd International Symposium on Information Theory. Academiai Kiadó, Budapest, pp. 267 281.

Aldabaa, A. A. A., Weindorf, D. C., Chakraborty, S., Sharma, A., Li, B., 2015. Combination of proximal and remote sensing methods for rapid soil salinity quantification. Geoderma 239-240, 34-46.

ASTM, 2013. Standard test method for laboratory weathering of solid materials using a humidity cell. Method D5744-13. Available online at: https://www.astm.org/Standards/D5744.htm (verified 3 Jul. 2017).

Auchmoody, L. R., Walters, R. S., 1988. Revegetation of a brine-killed forest site. Soil Sci. Soc. Am. J. 52, 277-280.

Berg, M., Tran, H. C., Nguyen, T. C., Pham, H. V., Schertenleib, R., Giger, W., 2001. Arsenic contamination of groundwater and drinking water in Vietnam: A human health threat. Environmental Science & Technology 35(13), 2621-2626.

Barreiros, M. A., Carvalho, M. L., Costa, N. M., Margues, M. I., Ramos, M. T., 1997. Application of total-reflection XRF to elemental studies of drinking water, X-Ray Spectrom. 26, 165-168.

Bettinelli, M., Beone, G. M., Spezia, S., Baffi, C., 2000. Determination of heavy metals in soils and sediments by microwave-assisted digestion and inductively coupled plasma optical emission spectrometry analysis. Analytica Chimica Acta 424, 289-296.

Box, G. E. P., Cox, D. R., 1964. An analysis of transformations. J. R. Stat. Soc. Series B Stat. Methodol. 26, 211-252.

Brevik, E. C., Sauer, T. J., 2015. The past, present, and future of soils and human health studies. Soil 1, 35-46. http://dx.doi.org/10.5194/soil-1-35-2015.

Chakraborty, S., Weindorf, D. C., Weindorf, C. A., Das, B. S., Li, B., Duda, B., Pennington, S., Ortiz, R., 2017a. Semi-quantitative evaluation of secondary carbonates via portable X-ray fluorescence spectrometry. Soil Sci. Soc. Am. J. 81, 844-852.

Chakraborty, S., B. Li, S. Deb, S. Paul, D. C. Weindorf, and B. S. Das. 2017a. Predicting soil arsenic pools by visible near infrared diffuse reflectance spectroscopy. Geoderma 296, 30-37.

Chakraborty, S., Weindorf, D. C., Deb, S., Li, B., Paul, S., Choudhury, A., Ray, D. P., 2017b. Rapid assessment of regional soil arsenic pollution risk via diffuse reflectance spectroscopy. Geoderma 289, 72-81.

Chang, C., Laird, D. A., Mausbach, M. J., Hurburgh, C. R., 2001. Near infrared reflectance spectroscopy: principal components regression analysis of soil properties. Soil Sci. Soc. Am. J. 65, 480-490.

Clark, J. J., Knudsen, A. C., 2014. Extent, characterization, and sources of soil lead contamination in small-urban residential neighborhoods.). Environ. Qual. 42, 1498-1506.

Eksperiandova, L. P., Blank, A. B., Makarovskaya, Y. N., 2002. Analysis of waste water by x-ray fluorescence spectrometry. X-Ray Spectrometry 31 (3), 259-263.

Gazley, M. F., Fisher, L. A., 2014. A review of the reliability and validity of portable X-ray fluorescence spectrometry (pXRF) data. In: Monograph 23, Mineral Resource and Ore Reserve Estimation, second edition AusIMM, pp. 69-82.

Hanna-Attisha, M., LaChance, J., Sadler, R. C., Schnepp, A. C., 2016. Elevated blood lead levels in children associated with the Flint drinking water crisis: A spatial analysis of risk and public health response. American Journal of Public Health 106(2), 283-290.

Institute for Advanced Sustainability Studies, 2012. Soil Contamination: A Severe Risk for the Environment and Human Health. IASS special publication, p. 5.

Kar, D., Sur, P., Mandal, S. K., Saha, T., Kole, R. K., 2008. Assessment of heavy metal pollution in surface water. International Journal of Environmental Science & Technology 5(1), 119-124.

Koch, J., Chakraborty, S., Li, B., Kucera, J. M., Deventer, P. V., Daniell, A., Faul, C., Man, T., Pearson, D., Duda, B., Weindorf, C. A., Weindorf, D. C., 2017. Proximal sensor analysis of mine tailings in South Africa: An exploratory study. Journal of Geochemical Exploration (Accepted; In Press) https://doi.org/10.1016/j.gexplo.2017.06.020.

Kuo, S., 1996. Phosphorus. In: Sparks et al. (Eds.), Methods of Soil Analysis—Part 3, Chemical Methods. Soil Science Society of America, Madison, Wis., pp. 869-919.

McGladdery, C., Weindorf, D. C., Chakraborty, S., Li, B., Paulette, L., Podar, D., Pearson, D., Kusi, N. Y. O., Duda, B., 2018. Elemental assessment of vegetation via portable Xray fluorescence (PXRF) spectrometry. J. Environ. Manage. (Accepted; In Press).

McLaren, T. I., Guppy, C. N., Tighe, M. K., Forster, N., Grave, P., Lisle, L. M., Bennett, J. W., 2012a. Rapid, nondestructive total elemental analysis of Vertisol soils using portable X-ray fluorescence. Soil Sci. Soc. Am. J. 76, 1436-1445.

McLaren, T. I., Guppy, C. N., Tighe, M. K., 2012. A rapid and nondestructive plant nutrient analysis using portable X-ray fluorescence. Soil Sci. Soc. Am. J. 76, 1446-1453.

Moncur, M. C., Ptacek, C. J., Lindsay, M. B. J., Blowes, D. W., Jambor, J. L., 2015. Long-term mineralogical and geochemical evolution of sulfide-rich mine tailings under a shallow water cover. Appl. Geochem. 57, 178-193.

Muggeo, V. M. R., 2008. Segmented: an R package to tit regression models with broken-line relationships. R News 8 (1), 20-25.

Muhammad, S., Shah, M. T., Khan, S., 2011. Health risk assessment of heavy metals and their apportionment in drinking water of Kohistan region, northern Pakistan. Michochemical Journal 98, 334-343.

Nordstrom, D. K., 2002. Worldwide occurrences of arsenic in ground water. Science 296 (5576), 2143-2145.

O'Rourke, S. M., Stockmann, U., Holden, N. M., McBratney, A. B., Minasny, B., 2016. An assessment of model averaging to improve predictive power of portable vis-NIR and XRF for the determination of agronomic soil properties. Geoderma 279, 31-44.

Paulette, L., Man, T., Weindorf, D. C., Person, T., 2015. Rapid assessment of soil and contaminant variability via portable x-ray fluorescence spectroscopy: Cop a Mica, Romania. Geoderma 243-244, 130-140.

Pearson, D., Chakraborty, S., Duda, B., Li, B., Weindorf, D. C., Deb, S., Brevik, E., Ray, D. P., 2017. Water analysis via portable X-ray fluorescence spectrometry. Journal of Hydrology 544, 172-179.

Peinado, F. M., Ruano, S. M., Gonzalez, M. G. B., Molina, C. E., 2010. A rapid field procedure for screening trace elements in polluted soil using portable X-ray fluorescence (PXRF). Geoderma 159, 76-82.

Pen-Mouratov, S., Shukurov, N., Steinberger, Y., 2008. Influence of Industrial heavy metal pollution on soil free-living nematode population. Environ. Pollut. 152, 172-183.

R Development Core Team, 2014. R: A Language and Environment for Statistical Computing. R Found. Stat. Comput, Vienna, Austria (Available online with updates at <http://www.cran.r-project.org>, Verified on Jan. 6, 2017).

Razo, I., Carrizales, L., Castro, J., Diaz-Barriga, F., Monroy, M., 2004. Arsenic and heavy metal pollution of soil, water, and sediments in a semi-arid climate mining area in Mexico. Water, Air, and Soil Pollution 152, 129-152.

Reidinger, S., Ramsey, M. H., Hartley, S. E., 2012. Rapid and accurate analyses of silicon and phosphorus in plants using a portable X-ray fluorescence spectrometer. New Phytologist 195, 699-706. Rengasamy, P., 2006. World salinization with emphasis on Australia. J. Exp. Bot. 57, 1017-1023.

Rhoades, J. D., 1996. Salinity: electrical conductivity and total dissolved solids. In: Sparks et al. (Eds.), Methods of Soil Analysis—Part 3, Chemical Methods. Soil Science Society of America, Madison, Wis., pp. 417-435.

Rodriguez-Freire, L., Avasarala, S., Ali, A. M. S., Agnew, D., Hoover, J. H., Artyushkova, K., Latta, D. E., Peterson, E. J., Lewis, J., Crossey, L. J., Brearley, A. J., Cerrato, J. M., 2016. Post Gold King Mine spill investigation of metal stability in water and sediments of the Animas River watershed. Environmental Science and Technology 50, 11539-11548.

Royal Society of Chemistry, 2009. Portable X-ray fluorescence analysis. Analytical Methods Committee Technical Brief No. 41. Available online at http://www.rsc.org/images/portable-x-ray-fluorescence-analysis-technical-brief-41_tcm18-214830.pdf (verified 3 Jan. 2018). Sacristán, D., Viscarra Rossel, R. A., Recatalá, L., 2016. Proximal sensing of Cu in soil and lettuce using portable X-ray fluorescence spectrometry. Geoderma 265, 6-11.

Salinity Laboratory Staff, 1954. Diagnosis and Improvement of Saline and Alkali Soils. Agricultural Handbook No. 60. US Department of Agriculture, Washington, D.C.

Savitzky, A., Golay, M. J. E., 1964. Smoothing and differentiation of data by simplified least squares procedures, Anal. Chem. 36, 1627-1639.

Sharma, A., Weindorf, D. C., Man, T., Aldabaa, A., Chakraborty, S., 2014. Characterizing soils via portable X-ray fluorescence spectrometer: 3. Soil reaction (pH). Geoderma 232-234, 141-147.

Sharma, A., Weindorf, D. C., Wang, D. D., Chakraborty, S., 2015. Characterizing soils via portable X-ray fluorescence spectrometer: 4. Cation exchange capacity (CEC). Geoderma 239-240, 130-134.

Simon, M., Ortiz, I., Garcia, I., Fernandez, J., Dorronsoro, C., Aguilar, J., 1999. Pollution of soils by the toxic spill of a pyrite mine (Aznalcollar, Spain). Science of the Total Environment 242, 105-115.

Soil Survey Staff, 2014. Soil survey field and laboratory methods manual Soil Survey Investigations Report No. 51, Version 2. USDA-NRCS, Lincoln, Nebr.

Soltanpour, P. N., Johnson, G. W., Workman, S. M., Jones, J. B., Miller, R. O., 1996. Inductively coupled plasma emission spectrometry and Inductively couple plasma-mass spectrometry. In: Sparks et al. (Eds.), Methods of Soil Analysis—Part 3, Chemical Methods. Soil Science Society of America, Madison, Wis., pp. 91-139.

Swanhart, S., Weindorf, D. C., Chakraborty, S., Bakr, N., Zhu, Y., Nelson, C., Shook, K., Acree, A., 2014. Soil salinity measurement via portable X-ray fluorescence spectrometry. Soil Sci. 179 (9). 417-423.

Trujillo-González, J. M., Torres-Mora, M. A., Keesstra, S., Brevik. E. C., Ballesta, R. J., 2016. Heavy metal accumulation related to population density in road dust samples taken from urban sites under different land uses. Sci. Total Environ. 553, 636-642.

United Nations—Food and Agricultural Organization, 2016. Extent or salt-affected soils. Available at <http://www-.fao.org/soils-portal/manejo-del-suelo/manejo-de-suelos-problematicos/suelos-arectados-por-salinidad/more-in-formationon-salt-affected-soils/es/> (verified 10 Mar. 2016).

US Environmental Protection Agency (US-EPA). 2007. Field portable X-ray fluorescence spectrometry for the determination of elemental concentrations in soil and sediment. Available online at: https://www.epa.gov/sites/production/files/2015-12/documents/6200.pdf (verified 20 Sep. 2016).

Vidakovic-Cifrek, Z., Pavlica, M., Regula, I., Papes, D., 2002. Cytogenetic damage in shallot (*Allium cepa*) root meristems induced by oil industry "high-density brines". Arch. Environ. Contam. Toxicol. 43, 284-291.

Weil, R. R., Brady, N. C., 2017. The nature and properties of soils. $15^{th}$ ed. Pearson, N.Y. 1086 pp.

Weindorf, D. C., Chakraborty, S., 2016. Portable X-ray fluorescence spectrometry analysis of soils. In: Hirmas, D. (Ed.). Methods of soil analysis. Soil Science Society of America, Madison, Wis. p. 1-8. doi:10.2136/methods-soil.2015.0033.

Weindorf, D. C., Bakr, N., Zhu, Y., 2014. Advances in portable X-ray fluorescence (PXRF) for environmental, pedological, and agronomic applications. Advances in Agronomy 128, 1-45.

Weindorf, D. C., Paulette, L., Man, T., 2013a. In-situ assessment of metal contamination via portable X-ray fluorescence spectroscopy: Zlatna, Romania. Environmental Pollution 182, 92-100.

Weindorf, D. C., Herrero, J., Castafieda, C., Bakr, N., Swanhart, S., 2013b. Direct soil gypsum quantification via portable X-ray fluorescence spectrometry. Soil Sci. Soc. Am. j. 77, 2071-2077.

Weindorf, D. C., Bakr, N., Zhu, Y., 2014. Advances in portable X-ray fluorescence (PXRF) for environmental, pedological, and agronomic applications. Adv. Agron. 128, 1-45.

Weindorf, D. C., Zhu, Y., Haggard, B., Lofton, J., Chakraborty, S., Bakr, N., Zhang, W., Weindorf, W. C., Legoria, M., 2012. Enhanced pedon horizonation using portable X-ray fluorescence spectroscopy. Soil Sci. Soc. Am. J. 76 (2), 522-531.

Weil, R. R., Brady, N. C., 2017. The nature and properties of soils, 15th ed. Pearson, N.Y., pp. 1086.

World Health Organization., 2008. Guidelines for drinking-water quality. WHO Press, World Health Organization, Geneva, Switzerland.

Wright, R. J., Stuczynski, T., 1996. Atomic absorption and name emission spectrometry. In: Sparks et al. (Eds.), Methods or Soil Analysis—Part 3, Chemical Methods. Soil Science Society or America, Madison, Wis., pp. 65-90.

Zhu, Y., Weindorf, D. C., Zhang, W., 2011. Characterizing soils using a portable x-ray fluorescence spectrometer: 1. Soil texture. Geoderma 167-168, 167-177.

What is claimed is:

1. A computerized method for determining metal content of a liquid sample comprising:
providing a portable x-ray fluorescence (PXRF) spectrometer, a probe connected to the PXRF spectrometer, one or more processors communicably coupled to the PXRF spectrometer, and one or more input/output interfaces communicably coupled to the one or more processors;
scanning the liquid sample using the PXRF spectrometer;
receiving a PXRF spectra from the PXRF spectrometer;
baseline correcting and smoothing the received PXRF spectra;
extracting a Kα emission line of one or more elements from the baseline corrected and smoothed PXRF spectra using only one beam from the PXRF spectrometer;
determining the metal content of the liquid sample using the one or more processors and a predictive model that relates the Kα emission line of the one or more elements to the metal content of the liquid sample; and
providing the metal content of the liquid sample to the one or more input/output interfaces.

2. The method as recited in claim 1, further comprising selecting the one or more element from a list of elements detectable by the PXRF spectrometer.

3. The method as recited in claim 2, wherein the selected elements are one or more of Ca, Cu, Fe, K, Mn, Pb and Zn.

4. The method as recited in claim 1, wherein the predictive model uses a partial least squares regression (PLSR) multivariate algorithm or a support vector regression (SVR) multivariate algorithm.

5. The method as recited in claim 1, wherein the predictive model relates the Kα emission line of the one or more elements to the metal content of the liquid sample by:
calculating a full width at half maximum (FWHM) and a maximum height ($H_{max}$) of each element peak using the Kα emission line for the element; and
using the calculated FWHM and $H_{max}$ for each element peak to predict the metal content of the liquid sample.

6. The method as recited in claim 1, further comprising placing the probe in contact with or proximate to the liquid sample.

7. The method as recited in claim 1, further comprising calibrating the predictive model.

8. The method as recited in claim 1, further comprising configuring the PXRF spectrometer to detect the metal content of the liquid sample.

9. The method as recited in claim 1, wherein the scanning, receiving, baseline correcting and smoothing, extracting, determining and providing steps are performed in situ.

10. The method as recited in claim 1, further comprising determining a geographic location of the liquid sample using a space-based satellite navigation system.

11. The method as recited in claim 1, further comprising determining an elevation of the liquid sample.

12. The method as recited in claim 1, wherein the scanning, receiving, baseline correcting and smoothing, extracting, determining and providing steps are performed on site proximate to where the liquid sample was taken.

13. The method as recited in claim 1, wherein the x-ray fluorescence (PXRF) spectrometer, the probe, the one or more processors, and the one or more input/output interfaces are integrated into a portable device.

14. An apparatus comprising:
a probe;
a portable x-ray fluorescence (PXRF) spectrometer connected to the probe;
one or more processors communicably coupled to the PXRF spectrometer;
one or more input/output interfaces communicably coupled to the one or more processors; and
the one or more processors scan the liquid sample using the PXRF spectrometer, receiving a PXRF spectra from the PXRF spectrometer, baseline correct and smooth the received PXRF spectra, extract a Kα emission line of one or more elements from the baseline corrected and smoothed PXRF spectra using only one beam from the PXRF spectrometer, determine the metal content of the liquid sample and a predictive model that relates the Kα emission line of the one or more elements to the metal content of the liquid sample, and provide the one or more properties of the liquid sample to the one or more input/output interfaces.

15. The apparatus as recited in claim 14, wherein the one or more processors further select the one or more element from a list of elements detectable by the PXRF spectrometer.

16. The apparatus as recited in claim 15, wherein the selected elements are one or more of Ca, Cu, Fe, K, Mn, Pb and Zn.

17. The apparatus as recited in claim 14, wherein the predictive model uses a partial least squares regression (PLSR) multivariate algorithm or a support vector regression (SVR) multivariate algorithm.

18. The method as recited in claim 14, wherein the predictive model relates the Kα emission line of the one or more elements to the metal content of the liquid sample by:
calculating a full width at half maximum (FWHM) and a maximum height ($H_{max}$) of each element peak using the Kα emission line for the element; and
using the calculated FWHM and $H_{max}$ for each element peak to predict the metal content of the liquid sample.

19. The apparatus as recited in claim 14, wherein the one or more processors further calibrate the predictive model.

20. The apparatus as recited in claim 14, wherein the one or more processors configure the PXRF spectrometer to detect the metal content of the liquid sample.

21. The apparatus as recited in claim 14, wherein the one or more processors perform the scanning, receiving, baseline correcting and smoothing, extracting, determining and providing steps in situ.

22. The apparatus as recited in claim 14, wherein the one or more processors further determine a geographic location of the liquid sample using a space-based satellite navigation system.

23. The apparatus as recited in claim 14, wherein the one or more processors further determine an elevation of the liquid sample.

24. The apparatus as recited in claim 14, wherein the one or more input/output interfaces comprise a display, a data storage, a printer or a communications interface.

25. The apparatus as recited in claim 14, wherein the apparatus is portable.

26. The apparatus as recited in claim 14, wherein are apparatus is used on site proximate to where the liquid sample was taken.

27. A computer program embodied on a non-transitory computer readable medium that causes one or more processors to:
   scan a liquid sample using a portable x-ray fluorescence (PXRF) spectrometer;
   receive a PXRF spectra from the PXRF spectrometer;
   baseline correct and smooth the received PXRF spectra;
   extract a $K\alpha$ emission line of one or more elements from the baseline corrected and smoothed PXRF spectra using only one beam from the PXRF spectrometer;
   determine a metal content of the liquid sample using the one or more processors and a predictive model that relates the $K\alpha$ emission line of the one or more elements to the metal content of the liquid sample; and
   provide the metal content of the liquid sample to one or more input/output interfaces.

* * * * *